US006911071B2

(12) United States Patent
Honan et al.

(10) Patent No.: US 6,911,071 B2
(45) Date of Patent: Jun. 28, 2005

(54) PHOTOGRAPHIC ELEMENT CONTAINING ACID PROCESSED GELATIN

(75) Inventors: James S. Honan, Spencerport, NY (US); Andrew M. Howe, Watford (GB); Paul A. Corbelli, LeRoy, NY (US); Lloyd A. Lobo, Webster, NY (US); Ryan B. Adams, Reston, VA (US); John S. Brand, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/836,901

(22) Filed: Apr. 30, 2004

(65) Prior Publication Data

US 2004/0202948 A1 Oct. 14, 2004

Related U.S. Application Data

(62) Division of application No. 10/140,846, filed on May 8, 2002.

(51) Int. Cl.[7] .......................... G03C 1/047; G03C 1/38; C12P 21/06; C09H 3/00; C07K 1/00

(52) U.S. Cl. ............................... 106/124.7; 106/160.1; 430/642; 430/636; 530/354; 530/355

(58) Field of Search .......................... 430/642, 96, 539, 430/201, 636; 106/124.7, 160.1; 530/534, 535; 347/105

(56) References Cited

U.S. PATENT DOCUMENTS

| | | | |
|---|---|---|---|
| 3,514,518 | A | 5/1970 | Charier-Vadrot |
| 3,551,151 | A | 12/1970 | Malan |
| 4,146,398 | A | 3/1979 | Arase et al. |
| 4,266,010 | A | 5/1981 | Nagatomo et al. |
| 4,301,238 | A | 11/1981 | Miyazawa et al. |
| 4,396,709 | A | 8/1983 | Kameoka et al. |
| 4,497,893 | A | 2/1985 | Deguchi et al. |
| 4,510,228 | A | 4/1985 | Tsubai et al. |
| 4,547,798 | A | 10/1985 | Matsumoto et al. |
| 4,605,609 | A | 8/1986 | Okazaki et al. |
| 4,606,985 | A | 8/1986 | Takaya et al. |
| 4,824,939 | A | 4/1989 | Simpson |
| 4,830,948 | A | 5/1989 | Ishikawa et al. |
| 5,024,932 | A | 6/1991 | Tanji et al. |
| 5,206,120 | A | 4/1993 | Hayashi |
| 5,206,128 | A | 4/1993 | Arai |
| 5,227,285 | A | 7/1993 | Hattori et al. |
| 5,326,686 | A | 7/1994 | Katoh et al. |
| 5,374,510 | A | 12/1994 | Westfal et al. |
| 5,484,598 | A | 1/1996 | Schurig et al. |
| 5,496,691 | A | 3/1996 | Miyamoto et al. |
| 5,508,142 | A | 4/1996 | Coppens et al. |
| 5,552,258 | A | 9/1996 | Macioch |
| 5,603,952 | A | 2/1997 | Soper |
| 5,620,830 | A | 4/1997 | Coppens et al. |
| 5,731,134 | A | 3/1998 | Honan et al. |
| 5,738,932 | A | 4/1998 | Kondo et al. |
| 5,882,846 | A | 3/1999 | Vacca et al. |
| 5,916,673 | A | 6/1999 | Fryberg et al. |
| 5,998,120 | A | 12/1999 | Connelly et al. |
| 6,037,451 | A | 3/2000 | Rowlands |
| 6,054,223 | A | 4/2000 | Tsuchiya et al. |
| 6,090,915 | A | 7/2000 | Herreid |
| 6,136,519 | A | 10/2000 | Hasebe |
| 6,258,517 | B1 | 7/2001 | Qiao et al. |
| 6,344,437 | B1 | 2/2002 | Takada et al. |
| 2001/0024678 | A1 | 9/2001 | Scott et al. |
| 2002/0142368 | A1 | 10/2002 | Miladinov et al. |
| 2003/0024353 | A1 | 2/2003 | Lobo et al. |
| 2003/0044456 | A1 | 3/2003 | Ichie et al. |

FOREIGN PATENT DOCUMENTS

| | | |
|---|---|---|
| GB | 1201940 | 8/1970 |
| GB | 1 483 551 | 8/1977 |
| GB | 1 489 080 | 10/1977 |
| JP | 00125775 A | 5/2000 |

OTHER PUBLICATIONS

P.I. Rose, *The Theory Of Photographic Process*, 4th Edition, edited by T.H. James (Macmillan Publishing Company, New York, 1977) pp. 51–67.
Japanese Patent Abstract 09304899.
Japanese Patent Abstract 09073154.
Japanese Patent Abstract 08262622.
Japanese Patent Abstract 07020593.
Japanese Patent Abstract 04163445.
Japanese Patent Abstract 04125550.
Japanese Patent Abstract 04005650.
Japanese Patent Abstract 01063950.
Japanese Patent Abstract 63259652.
Japanese Patent Abstract 62139550.
Japanese Patent Abstract 61177447.
Japanese Patent Abstract 61075345.
Japanese Patent Abstract 02042955.
Japanese Patent Abstract 2000201649.
Greser E: "Preparation of poultry gelatin", FSTA XP002213230 abstract.
Rother J: :Edible Gelatin Types, Properties, Use And Application In The Food Industry, Food Tech Europe, XX, XX, pp. 32, 34, 36, 38, XP002058982.
Maria Certad, Betty Perez: "Characteristics of Chicken Leg Gelatin Obtained Through an Acid Process", XP002249114 Abstract.

*Primary Examiner*—Richard L. Schilling
(74) *Attorney, Agent, or Firm*—Lynne M. Blank

(57) ABSTRACT

The present invention relates to an imaging member comprising poultry gelatin. In one embodiment, the poultry gelatin is located preferably in at least one layer in the upper half of said imaging member comprising poultry gelatin. Another embodiment provides an aqueous coating composition comprising poultry gelatin.

26 Claims, No Drawings

PHOTOGRAPHIC ELEMENT CONTAINING ACID PROCESSED GELATIN

CROSS-REFERENCE TO RELATED APPLICATION

This is a Divisional of Application No. U.S. Ser. No. 10/140,846 filed May 8, 2002, now allowed.

FIELD OF THE INVENTION

The present invention relates to imaging elements containing poultry gelatins.

BACKGROUND OF THE INVENTION

Imaging elements, particularly photographic silver halide imaging elements, commonly use a hydrophilic colloid as a film forming binder for layers thereof. The binder of choice in most cases is gelatin, prepared from various sources of collagen, most commonly osseine (see, e.g., P. I. Rose, The Theory of Photographic Process, 4th Edition, edited by T. H. James (Macmillan Publishing Company, New York, 1977) p. 51–65). The binder is expected to provide several functions, primarily to provide an element with some level of mechanical integrity and contain all the materials within the imaging element, which are required to provide an image. In particular, in photographic elements, the binder is expected to facilitate the diffusion of materials into and out of the element during a wet processing step. Gelatin is particularly suitable to perform this function, since it can absorb water and swell during the processing steps. In addition, gelatin also forms a cross linked network below a critical setting temperature through hydrogen bonding, which prevents dissolution of the gelatin when wet. However, most photoprocessing operations are carried out above the critical temperature, which would thereby melt the gelatin in a non-crosslinked form. In order to prevent the dissolution of the gelatin during the photoprocessing operation, the gelatin is crosslinked chemically, with a hardener, during the manufacture of the imaging element.

Imaging elements using gelatin as the binder are typically prepared by first dissolving gelatin in water. Other photographically useful materials may be added to the aqueous gelatin solution to complete the aqueous coating solution. These aqueous coating solutions are then coated on a support, as single or multiple layers, coated simultaneously or in sequence. The aqueous gelatin layers are dried in a drying section of the coating machine. Rose notes in the aforementioned reference that gelatin layers swell in water upon processing, and that stresses associated with the swelling process must be relieved. Because the layers are bound to the support, vertical swelling is the most important mechanism for relieving these stresses, since the layers are not free to swell laterally. Depending upon the conditions used to dry the gelatin layers of the imaging element, large lateral stresses can be induced, which upon processing, can result in buckling of the layers. This buckling occurs in an irregular pattern known as reticulation (P. I. Rose, The Theory of Photographic Process, 4th Edition, edited by T. H. James (Macmillan Publishing Company, New York, 1977) p. 62–63). In the final image, reticulation is manifested as lower gloss and higher haze in the final processed image, decreasing the commercial value.

High purity gelatins are generally required for imaging applications. Gelatins are made from sources of collagen. The collagen may be obtained from many sources known in the art, such as bones and hides. Bovine bones and pig skins are most commonly used.

The most commonly employed manufacturing process for obtaining high purity gelatins involves demineralization of a collagen containing material, typically cattle bone. The demineralized bone is known as osseine. This step is then followed by extended alkaline treatment (liming) and finally gelatin is extracted with water of increasing temperature as described in U.S. Pat. Nos. 3,514,518 and 4,824,939. The gelatin produced by this process, commonly referred to as lime processed osseine gelatin, has existed with various modifications throughout the gelatin industry for a number of years. The liming step of this process requires up to 60 days or more, the longest step in the approximately 3 month process of producing gelatin. The hydrolyzed collagen is extracted in a series of steps to obtain several gelatin fractions with varying molecular weights. In order to obtain gelatin of desired molecular weight to provide suitable coating solution viscosities, these fractions can be further hydrolyzed by high temperature hydrolysis. The fractions are then blended to obtain the appropriate molecular weight for photographic use.

Due to the length of time required to lime-process, acid-treatment of osseine may alternatively be employed. In the manufacture of acid processed osseine (APO), extractions begin immediately after demineralization and removal of excess acid, omitting the liming step. The gelatin is extracted in water at an acidic pH, in a series of fractions obtained at increasing temperatures. The acid processing of gelatin coincides with the lime processing of gelatin, except with respect to the liming step. The time required to prepare the osseine for gelatin extraction is reduced to about three days. Gelatins produced from acid-treatment exhibit different properties from lime-processed gelatins, especially the isoelectric point and gel strength.

The physical properties of gelatin, such as the isoelectric point (pI), which is the pH at which the gelatin exhibits a neutral charge, and gel strength or bloom, which is the weight in grams required to depress a plunger of 0.5 inch diameter (1.27 cm), with a $\frac{1}{64}^{th}$ inch (0.38 cm) radius of curvature at the bottom by 4 mm measured for a 6.16% dry weight gelatin after 24 hours hold at 10.0° C., depend upon the nature of the processing, such as lime or acid, as discussed above. The liming process results in extensive alkaline deamidation of the amides, glutamine and asparagine, to the corresponding acids, glutamic and aspartic acid, increasing the net negative charge on the protein. It has generally been noted that the pI of lime processed osseine (LPO) gelatin is typically in the range of approximately pH 4.7–5.3. Acid processed osseine (APO) gelatins typically exhibit higher pI values than lime processed gelatins. Acid processed cattle bones are typically in the range 6.0–8.5, while acid-processed pigskin (APP) gelatin is typically much higher, at around pH 9. While the use of acid processed gelatins in photographic elements offer a cost advantage, they may lead to undesirable photographic element layer coating properties.

The use of acid-processed gelatins in the uppermost layers of a photographic element can reduce the tendency to reticulation, as in U.S. Pat. No. 4,146,398. While an acid-processed gelatin is useful in a color photographic material, the use of acid-processed pigskin is undesirable due to the tendency to form coascervates, or slugs, with lime-processed gelatins. Instead, it is typical to use acid-processed bovine bone gelatins with isoelectric points of about 6.7–7.0. It has been observed that bovine acid-processed gelatins with even higher isoelectric points, in the range of 7.5–8.5, can provide even better resistance to reticulation, but results in the deterioration of other properties of interest.

One property, which suffers from the use of bovine acid-processed gelatins, is the tendency to viscosity increases with time in coating solutions. U.S. Pat. No. 5,998,120 discloses that solutions of pure APO gelatins in concentrated dispersions of photographically useful compounds leads to viscosity increases with time at standard operating temperatures. It has been found that this tendency is a property of acid-processed gelatins in general, and this tendency toward viscosity increases with time can be observed in coating solutions as well, which are typically more dilute and lower in viscosity than dispersions of photographically useful materials as described in 5,998,120. This tendency can complicate manufacturing conditions, such as requiring dilution of the gelatin containing coating solution or increased operating temperatures of the coating solutions. Such practices may result in undesired increased wet load, lower throughput, coating nonuniformity and chemical instability. The use of acid-processed gelatins with high isoelectric points, in the range of 7.5–8.5, can exacerbate this problem.

More recently, concerns about bovine spongiform encephalopathy (BSE or "Mad Cow Disease") have resulted in a reduced supply of cattle bone for producing both lime and acid-processed gelatins. Subsequent regulations on the production of gelatins for human consumption have created a need for new sources of gelatin for the production of imaging materials.

Problems to be Solved

It would be desirable to provide a non-bovine gelatin which provides reduced reticulation and improved robustness to drying, where higher temperatures or dilutions for managing viscosity increase with time are not necessary.

SUMMARY OF THE INVENTION

It is an object of the present invention to provide a non-bovine gelatin which provides reduced reticulation and improved robustness to drying, where higher temperatures or dilutions for managing viscosity increase with time are not necessarily employed. It is another object of the present invention to enable increase concentration of coating solutions.

This and other objects of the present invention are accomplished by providing an imaging member comprising poultry gelatin. In one embodiment, the poultry gelatin is located preferably in at least one layer in the upper half of said imaging member comprising poultry gelatin. Another embodiment provides an aqueous coating composition comprising poultry gelatin.

ADVANTAGEOUS EFFECT OF THE INVENTION

The present invention includes several advantages. The use of poultry gelatin in photographic elements, especially in the upper-most layers of the element provides increased gloss and reduced reticulation and haze. Also, poultry gelatins exhibit a lower tendency toward viscosity increases with time in coating solutions, such that more concentrated gelatin solutions can be made without the need to increase melt temperatures to manage the viscosity increase with time. The use of poultry gelatin also provides a gelatin free of BSE concerns and lower in cost.

DETAILED DESCRIPTION OF THE INVENTION

The preferred embodiment of the present invention provides an imaging member comprising poultry gelatin, preferably in at least one layer in the upper half of said imaging member comprising poultry gelatin, which provides enhanced reticulation. Poultry gelatins can be made from any number of foul bones, such as turkey, chicken, duck, goose, ostrich, quail, or emu. Preferred poultry for the production of gelatins are turkey and chicken, most preferably, turkey. The parts most typically used would be legs and feet, more preferrably, the bone connecting the portion referred to as the "drum stick" to the foot bones used for locomotion, which is typically discarded during processing.

Poultry gelatin can be produced using conventionally known processes for lime-processed or acid-processed gelatins. The poultry gelatin of the invention has a pI of greater than or equal to 4.9 to 9.5, preferably from 6.0–9.0, more preferably from 6.5–9.0, and most preferably about 7.5–9.0. The acid-processed poultry gelatin will typically have a range in pI from 6.0–9.0, whereas the lime-processed poultry gelatin will have a pI ranging from 4.9 up to 6.0.

High purity gelatins are generally required for imaging applications. Currently the most commonly employed manufacturing process for obtaining high purity gelatins involves demineralization with acid of a collagen containing material, typically cattle bone. The demineralized bone is known as osseine. This step is then followed by extended alkaline treatment (liming) and finally gelatin extractions with water of increasing temperature. The gelatin produced by this process, commonly referred to as lime processed osseine gelatin, has existed with various modifications throughout the gelatin industry for a number of years. The liming step of this process requires up to 60 days or more, the longest step in the approximately 3 month process of producing gelatin. The hydrolyzed collagen is extracted in a series of steps to obtain several gelatin fractions with varying molecular weights. In order to obtain gelatin of desired molecular weight to provide suitable coating solution viscosities, these fractions can be further hydrolyzed by high temperature hydrolysis. The fractions are then blended to obtain the appropriate molecular weight for photographic use.

Due to the length of time required to lime-process, acid-treatment of osseine may alternatively be employed. In acid processing, the osseine is washed free of excess acid immediately after demineralization. The stock is then loaded into extractors containing dilute acid. The gelatin is extracted from the stock during successive cooks at increasing temperatures. The extracted gelatin is pH adjusted, filtered, concentrated, demineralized and dried. The time required for liming is omitted and the time to prepare the osseine for gelatin extraction is reduced to about three days. Gelatins produced from acid-treatment typically exhibit different properties from lime-processed gelatins, especially the isoelectric point, as described in the following paragraph.

The physical properties of gelatin, such as the isoelectric point (designated pI, which is the pH at which the gelatin exhibits a neutral charge), molecular weight and molecular weight distribution depend upon the nature of the processing, such as lime or acid, as discussed above. It has generally been noted that the pI of lime processed osseine (LPO) gelatin is typically in the range of approximately pH 4.7–5.3. Acid processed osseine (APO) gelatins typically exhibit higher pI values than lime processed gelatins. Acid processed cattle bones are typically in the range 6.0–8.5, while acid-processed pigskin (APP) gelatin is typically much higher, at around pH 9. While the use of acid processed gelatins in photographic elements would offer a cost advantage, they generally exhibit lower than desired molecular weights for photographic use, as reducing the molecular weight (MW) of gelatin can lead to undesirable photographic element layer coating properties.

The preferred embodiment of the invention comprises an imaging member comprising poultry gelatin. The gelatin of the invention is preferably deployed in the upper layers of the imaging element. These layers will typically be the outermost layer, furthest from the support, and the three layers beneath the outermost layer, preferably the outermost layer and the two layers beneath the outermost layer, and most preferably, the outermost layer and the layer immediately below. In a photographic element, these most preferred layers typically constitute the overcoat and ultraviolet absorbing layer. In the case where the overcoat is a non-gelatin or low-gelatin containing layer comprising a water permeable polymeric overcoat which forms a water impermeable, stain-resistant overcoat after image processing, the gelatin of the invention is preferably employed in the three layers below, more preferably the two layers below, most preferably the layer immediately below. In an inkjet dye-receiving element, the upper layers constitute the image receiving layer and the layer immediately below it. Most preferably, the poultry gelatin is placed in the top layer of the imaging element As used herein the phrase "imaging element" is a material that may be used as a imaging support for the transfer of images to the support by techniques such as ink jet printing, thermal dye-sublimation printing, or electrophotographic printing as well as a support for silver halide images. As used herein, the phrase "photographic element" is a material that utilizes photosensitive silver halide in the formation of images.

The electrographic and electrophotographic processes and their individual steps have been well described in detail in many books and publications. The processes incorporate the basic steps of creating an electrostatic image, developing that image with charged, colored particles (toner), optionally transferring the resulting developed image to a secondary substrate, and fixing the image to the substrate. There are numerous variations in these processes and basic steps, the use of liquid toners in place of dry toners is simply one of those variations.

The first basic step, creation of an electrostatic image, can be accomplished by a variety of methods. The electrophotographic process of copiers uses imagewise photodischarge, through analog or digital exposure, of a uniformly charged photoconductor. The photoconductor may be a single-use system, or it may be rechargeable and reimageable, like those based on selenium or organic photoreceptors.

In an alternate electrographic process, electrostatic images are created ionographically. The latent image is created on dielectric (charge-holding) medium, either paper or film. Voltage is applied to selected metal styli or writing nibs from an array of styli spaced across the width of the medium, causing a dielectric breakdown of the air between the selected styli and the medium. Ions are created, which form the latent image on the medium.

Electrostatic images, however generated, are developed with oppositely charged toner particles. For development with liquid toners, the liquid developer is brought into direct contact with the electrostatic image. Usually a flowing liquid is employed, to ensure that sufficient toner particles are available for development. The field created by the electrostatic image causes the charged particles, suspended in a nonconductive liquid, to move by electrophoresis. The charge of the latent electrostatic image is thus neutralized by the oppositely charged particles. The theory and physics of electrophoretic development with liquid toners are well described in many books and publications.

If a reimageable photoreceptor or an electrographic master is used, the toned image is transferred to paper (or other substrate). The paper is charged electrostatically, with the polarity chosen to cause the toner particles to transfer to the paper. Finally, the toned image is fixed to the paper. For self-fixing toners, residual liquid is removed from the paper by air-drying or heating. Upon evaporation of the solvent these toners form a film bonded to the paper. For heat-fusible toners, thermoplastic polymers are used as part of the particle. Heating both removes residual liquid and fixes the toner to paper.

Ink jet images on a nacreous support are preferred as they provide a digital printing method that can be utilized in the home. The dye receiving layer (DRL), which may contain the gelatin of the present invention, may be applied by any known methods, such as solvent coating, or melt extrusion coating techniques. The DRL is coated over the tie layer (TL) at a thickness ranging from 0.1–10 $\mu$m, preferably 0.5–5 $\mu$m. There are many known formulations, which may be useful as dye receiving layers. The primary requirement is that the DRL is compatible with the inks which it will be imaged so as to yield the desirable color gamut and density. As the ink drops pass through the DRL, the dyes are retained or mordanted in the DRL, while the ink solvents pass freely through the DRL and are rapidly absorbed by the TL. Additionally, the DRL formulation is preferably coated from water, exhibits adequate adhesion to the TL, and allows for easy control of the surface gloss.

For example, Misuda et al. in U.S. Pat. Nos. 4,879,166, 5,264,275, 5,104,730, 4,879,166, and Japanese Patent Nos. 1,095,091, 2,276,671, 2,276,670, 4,267,180, 5,024,335, and 5,016,517 discloses aqueous based DRL formulations comprising mixtures of psuedo-bohemite and certain water soluble resins. Light, in U.S. Pat. Nos. 4,903,040, 4,930,041, 5,084,338, 5,126,194, 5,126,195, and 5,147,717 discloses aqueous-based DRL formulations comprising mixtures of vinyl pyrrolidone polymers and certain water-dispersible and/or water-soluble polyesters, along with other polymers and addenda. Butters et al. in U.S. Pat. Nos. 4,857,386 and 5,102,717 disclose ink-absorbent resin layers comprising mixtures of vinyl pyrrolidone polymers and acrylic or methacrylic polymers. Sato et al. in U.S. Pat. No. 5,194,317 and Higuma et al. in U.S. Pat. No. 5,059,983 disclose aqueous-coatable DRL formulations based on poly (vinyl alcohol). Iqbal, in U.S. Pat. No. 5,208,092, discloses water-based DRL formulations comprising vinyl copolymers, which are subsequently cross-linked. In addition to these examples, there may be other known or contemplated DRL formulations, which are consistent with the aforementioned primary and secondary requirements of the DRL.

The DRL may also contain varying levels and sizes of matting agents for the purpose of controlling gloss, friction, and/or fingerprint resistance, surfactants to enhance surface uniformity and to adjust the surface tension of the dried coating, mordanting agents, anti-oxidants, UV absorbing compounds, light stabilizers, and the like.

Although the ink-receiving elements as described above can be successfully used to achieve the objectives of the present invention, it may be desirable to overcoat the DRL for the purpose of enhancing the durability of the imaged element. Such overcoats may be applied to the DRL either before or after the element is imaged. For example, the DRL can be overcoated with an ink-permeable layer through which inks freely pass. Layers of this type are described in U.S. Pat. Nos. 4,686,118, 5,027,131, and 5,102,717. Alternatively, an overcoat may be added after the element is imaged. Any of the known laminating films and equipment may be used for this purpose. The inks used in the aforementioned imaging process are well known, and the ink formulations are often closely tied to the specific processes, i.e., continuous, piezoelectric, or thermal. Therefore, depending on the specific ink process, the inks may contain widely differing amounts and combinations of solvents, colorants, preservatives, surfactants, humectants, and the like. Inks preferred for use in combination with the image recording elements are water-based, such as those currently sold for use in the Hewlett-Packard Desk Writer 560C printer. However, it is intended that alternative embodiments of the image-recording elements as described above, which may be formulated for use with inks which are specific to a given ink-recording process or to a given commercial vendor, fall within the scope of the present invention.

Photographic imaging elements in accordance with specific embodiments of the present invention can be black and white, single color or multicolor photographic elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer. Depending upon the dye-image-providing material employed in the photographic element, it can be incorporated in the silver halide emulsion layer or in a separate layer associated with the emulsion layer. The dye-image-providing material can be any of a number known in the art, such as dye-forming couplers, bleachable dyes, dye developers and redox dye-releasers, and the particular one employed will depend on the nature of the element, and the type of image desired. Dye-image-providing materials employed with conventional color photographic materials designed for processing with a separate developing solution are preferably dye-forming couplers, i.e., compounds which couple with oxidized developing agent to form a dye.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support, which can be transparent or reflective (for example, a paper support). Photographic elements may also usefully include a magnetic recording material as described in Research Disclosure, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical. The present invention also contemplates the use of photographic imaging elements in accordance with of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

Silver halide used in photographic imaging elements may be silver iodobromide, silver bromide, silver chloride, silver chlorobromide, silver chloroiodobromide, silver iodochloride, and the like. For example, in one particular embodiment, the silver halide used in photographic imaging elements may contain at least 90 mol % silver chloride or more (for example, at least 95%, 98%, 99% or 100% silver chloride). The type of silver halide grains preferably include polymorphic, cubic, and octahedral. The grain size of the silver halide may have any distribution known to be useful in photographic compositions, and may be either polydispersed or monodispersed.

Tabular grain silver halide emulsions may also be used. Tabular grains are those with two parallel major faces each clearly larger than any remaining grain face (e.g., ECD/t is at least 2, where ECD is the diameter of a circle having an area equal to grain projected area and t is tabular grain thickness), and tabular grain emulsions are those in which the tabular grains account for at least 50 percent, preferably at least 70 percent and optimally at least 90 percent of total grain projected area. The tabular grains can account for substantially all (e.g., greater than 97 percent) of total grain projected area. The tabular grain emulsions can be high aspect ratio tabular grain emulsions—i.e., ECD/t>8, intermediate aspect ratio tabular grain emulsions—i.e., ECD/t=5 to 8, or low aspect ratio tabular grain emulsions—i.e., ECD/t=2 to 5. The emulsions preferably typically exhibit high tabularity (T), where T (i.e., $ECD/t^2$)>25 and ECD and t are both measured in micrometers (am). The tabular grains can be of any thickness compatible with achieving an aim average aspect ratio and/or average tabularity of the tabular grain emulsion. Preferably the tabular grains satisfying projected area requirements are those having thicknesses of <0.3 μm, thin (<0.2 μm) tabular grains being specifically preferred and ultrathin (<0.07 μm) tabular grains being contemplated for maximum tabular grain performance enhancements. When the native blue absorption of iodohalide tabular grains is relied upon for blue speed, thicker tabular grains, typically up to 0.5 μm in thickness, are contemplated. Tabular grains formed of silver halide(s) that form a face centered cubic (rock salt type) crystal lattice structure can have either {100} or {111} major faces.

Silver halide grains may be prepared according to methods known in the art, such as those described in Research Disclosure I and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

Silver halide grains may be advantageously subjected to chemical sensitization with noble metal (for example, gold)

sensitizers, middle chalcogen (for example, sulfur) sensitizers, reduction sensitizers and others known in the art. Compounds and techniques useful for chemical sensitization of silver halide are known in the art and described in Research Disclosure I and the references cited therein.

Photographic imaging elements provide the silver halide in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in Research Disclosure I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in Research Disclosure I. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30 to 80 C., as described in Research Disclosure I, Section IV (pages 510–511) and the references cited therein.

The silver halide may be sensitized by sensitizing dyes by any method known in the art, such as described in Research Disclosure I. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alcohol. The dye/silver halide emulsion may be mixed with a dispersion of color image-forming coupler immediately before coating or in advance of coating (for example, 2 hours).

Photographic imaging elements are preferably imagewise exposed using any of the known techniques, including those described in Research Disclosure I, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

In one embodiment, this invention is directed to a silver halide photographic element capable of excellent performance when exposed by either an electronic printing method or a conventional optical printing method. An electronic printing method comprises subjecting a radiation sensitive silver halide emulsion layer of a recording element to actinic radiation of at least $10^{-4}$ ergs/cm$^2$ for up to 100$\mu$ seconds duration in a pixel-by-pixel mode wherein the silver halide emulsion layer is comprised of silver halide grains as described above. A conventional optical printing method comprises subjecting a radiation sensitive silver halide emulsion layer of a recording element to actinic radiation of at least $10^{-4}$ ergs/cm$^2$ for $10^{-3}$ to 300 seconds in an imagewise mode wherein the silver halide emulsion layer is comprised of silver halide grains as described above.

This invention in a preferred embodiment utilizes a radiation-sensitive emulsion comprised of silver halide grains (a) containing greater than 50 mole percent chloride, based on silver, (b) having greater than 50 percent of their surface area provided by {100} crystal faces, and (c) having a central portion accounting for from 95 to 99 percent of total silver and containing two dopants selected to satisfy each of the following class requirements: (i) a hexacoordination metal complex which satisfies the formula $$[ML_6]^n \qquad (I)$$

wherein n is zero, −1, −2, −3 or −4, M is a filled frontier orbital polyvalent metal ion, other than iridium, and $L_6$ represents bridging ligands which can be independently selected, provided that least four of the ligands are anionic ligands, and at least one of the ligands is a cyano ligand or a ligand more electronegative than a cyano ligand, and (ii) an iridium coordination complex containing a thiazole or substituted thiazole ligand.

It has been unexpectedly discovered that significantly improved reciprocity performance can be obtained for silver halide grains (a) containing greater than 50 mole percent chloride, based on silver, and (b) having greater than 50 percent of their surface area provided by {100} crystal faces by employing a hexacoordination complex dopant of class (i) in combination with an iridium complex dopant comprising a thiazole or substituted thiazole ligand. The reciprocity improvement is obtained for silver halide grains employing conventional gelatino-peptizer, unlike the contrast improvement described for the combination of dopants set forth in U.S. Pat. Nos. 5,783,373 and 5,783,378, which requires the use of low methionine gelatino-peptizers as discussed therein, and which states it is preferable to limit the concentration of any gelatino-peptizer with a methionine level of greater than 30 micromoles per gram to a concentration of less than 1 percent of the total peptizer employed. It is specifically contemplated to use significant levels (i.e., greater than 1 weight percent of total peptizer) of conventional gelatin (e.g., gelatin having at least 30 micromoles of methionine per gram) as a gelatino-peptizer for the silver halide grains of the emulsions. In preferred embodiments of the invention, gelatino-peptizer is employed which comprises at least 50 weight percent of gelatin containing at least 30 micromoles of methionine per gram, as it is frequently desirable to limit the level of oxidized low methionine gelatin which may be used for cost and certain performance reasons.

In a specific, preferred form of the invention it is contemplated to employ a class (i) hexacoordination complex dopant satisfying the formula:

$$[ML_6]^n \qquad (I)$$

where n is zero, −1, −2, −3 or −4,

M is a filled frontier orbital polyvalent metal ion, other than iridium, preferably $Fe^{+2}$, $Ru^{+2}$, $Os^{+2}$, $Co^{+3}$, $Rh^{+3}$, $Pd^{+4}$ or $Pt^{+4}$, more preferably an iron, ruthenium or osmium ion, and most preferably a ruthenium ion, $L_6$ represents six bridging ligands which can be independently selected, provided that least four of the ligands are anionic ligands and at least one (preferably at least 3 and optimally at least 4) of the ligands is a cyano ligand or a ligand more electronegative than a cyano ligand. Any remaining ligands can be selected from among various other bridging ligands, including aquo ligands, halide ligands (specifically, fluoride, chloride, bromide and iodide), cyanate ligands, thiocyanate ligands, selenocyanate ligands, tellurocyanate ligands, and azide ligands. Hexacoordinated transition metal complexes of class (i) which include six cyano ligands are specifically preferred.

Illustrations of specifically contemplated class (i) hexacoordination complexes for inclusion in the high chloride grains are provided by Olm et al U.S. Pat. No. 5,503,970 and Daubendiek et al U.S. Pat. Nos. 5,494,789 and 5,503,971, and Keevert et al U.S. Pat. No. 4,945,035, as well as Murakami et al Japanese Patent Application Hei-2[1990]-249588, and *Research Disclosure* Item 36736. Useful neutral and anionic organic ligands for class (ii) dopant hexacoordination complexes are disclosed by Olm et al U.S. Pat. No. 5,360,712 and Kuromoto et al U.S. Pat. No. 5,462,849.

Class (i) dopant is preferably introduced into the high chloride grains after at least 50 (most preferably 75 and optimally 80) percent of the silver has been precipitated, but before precipitation of the central portion of the grains has been completed. Preferably class (i) dopant is introduced before 98 (most preferably 95 and optimally 90) percent of the silver has been precipitated. Stated in terms of the fully precipitated grain structure, class (i) dopant is preferably present in an interior shell region that surrounds at least 50 (most preferably 75 and optimally 80) percent of the silver and, with the more centrally located silver, accounts the entire central portion (99 percent of the silver), most preferably accounts for 95 percent, and optimally accounts for 90 percent of the silver halide forming the high chloride grains. The class (i) dopant can be distributed throughout the interior shell region delimited above or can be added as one or more bands within the interior shell region.

Class (i) dopant can be employed in any conventional useful concentration. A preferred concentration range is from $10^{-8}$ to $10^{-3}$ mole per silver mole, most preferably from $10^{-6}$ to $5\times10^{-4}$ mole per silver mole.

The following are specific illustrations of class (i) dopants:

(i-1) $[Fe(CN)_6]^{-4}$
(i-2) $[Ru(CN)_6]^{-4}$
(i-3) $[Os(CN)_6]^{-4}$
(i-4) $[Rh(CN)_6]^{-3}$
(i-5) $[Co(CN)_6]^{-3}$
(i-6) $[Fe(pyrazine)(CN)_5]^{-4}$
(i-7) $[RuCl(CN)_5]^{-4}$
(i-8) $[OsBr(CN)_5]^{-4}$
(i-9) $[RhF(CN)_5]^{-3}$
(i-10) $[In(NCS)_6]^{-3}$
(i-11) $[FeCO(CN)_5]^{-3}$
(i-12) $[RuF_2(CN)_4]^{-4}$
(i-13) $[OsCl_2(CN)_4]^{-4}$
(i-14) $[RhI_2(CN)_4]^{-3}$
(i-15) $[Ga(NCS)_6]^{-3}$
(i-16) $[Ru(CN)_5(OCN)]^{-4}$
(i-17) $[Ru(CN)_5(N_3)]^{-4}$
(i-18) $[Os(CN)_5(SCN)]^{-4}$
(i-19) $[Rh(CN)_5(SeCN)]^{-3}$
(i-20) $[Os(CN)Cl_5]^{-4}$
(i-21) $[Fe(CN)_3Cl_3]^{-3}$
(i-22) $[Ru(CO)_2(CN)_4]^{-1}$ When the class (i) dopants have a net negative charge, it is appreciated that they are associated with a counter ion when added to the reaction vessel during precipitation. The counter ion is of little importance, since it is ionically dissociated from the dopant in solution and is not incorporated within the grain. Common counter ions known to be fully compatible with silver chloride precipitation, such as ammonium and alkali metal ions, are contemplated. It is noted that the same comments apply to class (ii) dopants, otherwise described below.

The class (ii) dopant is an iridium coordination complex containing at least one thiazole or substituted thiazole ligand. Careful scientific investigations have revealed Group VIII hexahalo coordination complexes to create deep electron traps, as illustrated R. S. Eachus, R. E. Graves and M. T. Olm *J. Chem. Phys.*, Vol. 69, pp. 4580–7 (1978) and *Physica Status Solidi A*, Vol. 57, 429–37 (1980) and R. S. Eachus and M. T. Olm *Annu. Rep. Prog. Chem. Sect. C. Phys. Chem.*, Vol. 83, 3, pp. 3–48 (1986). The class (ii) dopants employed in the practice of this invention are believed to create such deep electron traps. The thiazole ligands may be substituted with any photographically acceptable substituent, which does not prevent incorporation of the dopant into the silver halide grain. Exemplary substituents include lower alkyl (e.g., alkyl groups containing 1–4 carbon atoms), and specifically methyl. A specific example of a substituted thiazole ligand, which may be used, is 5-methylthiazole. The class (ii) dopant preferably is an iridium coordination complex having ligands each of which are more electropositive than a cyano ligand. In a specifically preferred form the remaining non-thiazole or non-substituted-thiazole ligands of the coordination complexes forming class (ii) dopants are halide ligands.

It is specifically contemplated to select class (ii) dopants from among the coordination complexes containing organic ligands disclosed by Olm et al U.S. Pat. Nos. 5,360,712 and 5,457,021 and Kuromoto et al U.S. Pat. No. 5,462,849.

In a preferred form it is contemplated to employ as a class (ii) dopant a hexacoordination complex satisfying the formula:

$$[IrL^1_6]^{n'} \qquad (II)$$

wherein n' is zero, −1, −2, −3 or −4, and $L^1_6$ represents six bridging ligands which can be independently selected, provided that at least four of the ligands are anionic ligands, each of the ligands is more electropositive than a cyano ligand, and at least one of the ligands comprises a thiazole or substituted thiazole ligand. In a specifically preferred form at least four of the ligands are halide ligands, such as chloride or bromide ligands.

Class (ii) dopant is preferably introduced into the high chloride grains after at least 50 (most preferably 85 and optimally 90) percent of the silver has been precipitated, but before precipitation of the central portion of the grains has been completed. Preferably class (ii) dopant is introduced before 99 (most preferably 97 and optimally 95) percent of the silver has been precipitated. Stated in terms of the fully precipitated grain structure, class (ii) dopant is preferably present in an interior shell region that surrounds at least 50 (most preferably 85 and optimally 90) percent of the silver and, with the more centrally located silver, accounts the entire central portion (99 percent of the silver), most preferably accounts for 97 percent, and optimally accounts for 95 percent of the silver halide forming the high chloride grains. The class (ii) dopant can be distributed throughout the interior shell region delimited above or can be added as one or more bands within the interior shell region.

Class (ii) dopant can be employed in any conventional useful concentration. A preferred concentration range is from $10^{-9}$ to $10^{-4}$ mole per silver mole. Iridium is most preferably employed in a concentration range of from $10^{-8}$ to $10^{-5}$ mole per silver mole.

Specific illustrations of class (ii) dopants are the following:

(ii-1) $[IrCl_5(thiazole)]^{-2}$ (ii-2) $[IrCl_4(thiazole)_2]^{-1}$ (ii-3) $[IrBr_5(thiazole)]^{-2}$ (ii-4) $[IrBr_4(thiazole)_2]^{-1}$ (ii-5) $[IrCl_5(5\text{-methylthiazole})]^{-2}$ (ii-6) $[IrCl_4(5\text{-methylthiazole})_2]^{-1}$ (ii-7) $[IrBr_5(5\text{-methylthiazole})]^{-2}$ (ii-8) $[IrBr_4(5\text{-methylthiazole})_2]^{-1}$ In one preferred aspect in a layer using a magenta dye forming coupler, a class (ii) dopant in combination with an $OsCl_5(NO)$ dopant has been found to produce a preferred result.

Emulsions can be realized by modifying the precipitation of conventional high chloride silver halide grains having predominantly (>50%) {100} crystal faces by employing a combination of class (i) and (ii) dopants as described above.

The silver halide grains precipitated contain greater than 50 mole percent chloride, based on silver. Preferably the grains contain at least 70 mole percent chloride and, optimally at least 90 mole percent chloride, based on silver. Iodide can be present in the grains up to its solubility limit, which is in silver iodochloride grains, under typical conditions of precipitation, about 11 mole percent, based on silver. It is preferred for most photographic applications to limit iodide to less than 5 mole percent iodide, most preferably less than 2 mole percent iodide, based on silver.

Silver bromide and silver chloride are miscible in all proportions. Hence, any portion, up to 50 mole percent, of the total halide not accounted for chloride and iodide, can be bromide. For color reflection print (i.e., color paper) uses bromide is typically limited to less than 10 mole percent based on silver and iodide is limited to less than 1 mole percent based on silver.

In a widely used form high chloride grains are precipitated to form cubic grains—that is, grains having {100} major faces and edges of equal length. In practice ripening effects usually round the edges and corners of the grains to some extent. However, except under extreme ripening conditions substantially more than 50 percent of total grain surface area is accounted for by {100} crystal faces.

High chloride tetradecahedral grains are a common variant of cubic grains. These grains contain 6 {100} crystal faces and 8 {111} crystal faces. Tetradecahedral grains are within the contemplation of this invention to the extent that greater than 50 percent of total surface area is accounted for by {100} crystal faces.

Although it is common practice to avoid or minimize the incorporation of iodide into high chloride grains employed in color paper, it is has been recently observed that silver iodochloride grains with {100} crystal faces and, in some instances, one or more {111} faces offer exceptional levels of photographic speed. In the these emulsions iodide is incorporated in overall concentrations of from 0.05 to 3.0 mole percent, based on silver, with the grains having a surface shell of greater than 50 Å that is substantially free of iodide and a interior shell having a maximum iodide concentration that surrounds a core accounting for at least 50 percent of total silver. Such grain structures are illustrated by Chen et al EPO 0,718,679.

In another improved form the high chloride grains can take the form of tabular grains having {100} major faces. Preferred high chloride {100} tabular grain emulsions are those in which the tabular grains account for at least 70 (most preferably at least 90) percent of total grain projected area. Preferred high chloride {100} tabular grain emulsions have average aspect ratios of at least 5 (most preferably at least >8). Tabular grains typically have thicknesses of less than 0.3 μm, preferably less than 0.2 μm, and optimally less than 0.07 μm. High chloride {100} tabular grain emulsions and their preparation are disclosed by Maskasky U.S. Pat. Nos. 5,264,337 and 5,292,632, House et al U.S. Pat. No. 5,320,938, Brust et al U.S. Pat. No. 5,314,798, and Chang et al U.S. Pat. No. 5,413,904.

Once high chloride grains having predominantly {100} crystal faces have been precipitated with a combination of class (i) and class (ii) dopants described above, chemical and spectral sensitization, followed by the addition of conventional addenda to adapt the emulsion for the imaging application of choice can take any convenient conventional form. These conventional features are illustrated by *Research Disclosure*, Item 38957, cited above, particularly:

III. Emulsion washing,

IV. Chemical sensitization,

V. Spectral sensitization and desensitization,

VII. Antifoggants and stabilizers,

VIII. Absorbing and scattering materials,

IX. Coating and physical property modifying addenda, and

X. Dye image formers and modifiers.

Some additional silver halide, typically less than 1 percent, based on total silver, can be introduced to facilitate chemical sensitization. It is also recognized that silver halide can be epitaxially deposited at selected sites on a host grain to increase its sensitivity. For example, high chloride {100} tabular grains with corner epitaxy are illustrated by Maskasky U.S. Pat. No. 5,275,930. For the purpose of providing a clear demarcation, the term "silver halide grain" is herein employed to include the silver necessary to form the grain up to the point that the final {100} crystal faces of the grain are formed. Silver halide later deposited that does not overlie the {100} crystal faces previously formed accounting for at least 50 percent of the grain surface area is excluded in determining total silver forming the silver halide grains. Thus, the silver forming selected site epitaxy is not part of the silver halide grains while silver halide that deposits and provides the final {100} crystal faces of the grains is included in the total silver forming the grains, even when it differs significantly in composition from the previously precipitated silver halide.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895,826, 3,002,836, 3,034,892, 3,041,236, 4,883,746 and "Farbkuppler-Eine Literature Ubersicht," published in Agfa Mitteilungen, Band III, pp. 156–175 (1961). Preferably such couplers are phenols and naphthols that form cyan dyes on reaction with oxidized color developing agent. Also preferable are the cyan couplers described in, for instance, European Patent Application Nos. 491,197, 544,322, 556,700, 556,777, 565,096, 570,006, and 574,948.

Typical cyan couplers are represented by the following formulas:

CYAN-1

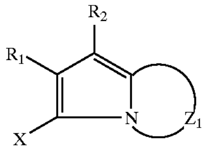

CYAN-2

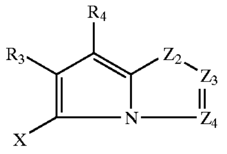

CYAN-3

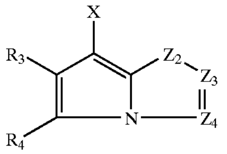

CYAN-4

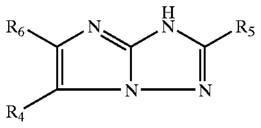

wherein $R_1$, $R_5$ and $R_8$ each represents a hydrogen or a substituent, $R_2$ represents a substituent, $R_3$, $R_4$ and $R_7$ each represent an electron attractive group having a Hammett's substituent constant $\sigma_{para}$ of 0.2 or more and the sum of the $\sigma_{para}$ values of $R_3$ and $R_4$ is 0.65 or more, $R_6$ represents an electron attractive group having a Hammett's substituent constant $\sigma_{para}$ of 0.35 or more, X represents a hydrogen or a coupling-off group, $Z_1$ represents nonmetallic atoms necessary for forming a nitrogen-containing, six-membered, heterocyclic ring which has at least one dissociative group, $Z_2$ represents —C($R_7$)= and —N=, and $Z_3$ and $Z_4$ each represent —C($R_8$)= and —N=.

For purposes of this invention, an "NB coupler" is a dye-forming coupler which is capable of coupling with the developer 4-amino-3-methyl-N-ethyl-N-(2-methanesulfonamidoethyl) aniline sesquisulfate hydrate to form a dye for which the left bandwidth (LBW) of its absorption spectra upon "spin coating" of a 3% w/v solution of the dye in di-n-butyl sebacate solvent is at least 5 nm less than the LBW for a 3% w/v solution of the same dye in acetonitrile. The LBW of the spectral curve for a dye is the distance between the left side of the spectral curve and the wavelength of maximum absorption measured at a density of half the maximum.

The "spin coating" sample is prepared by first preparing a solution of the dye in di-n-butyl sebacate solvent (3% w/v). If the dye is insoluble, dissolution is achieved by the addition of some methylene chloride. The solution is filtered and 0.1–0.2 ml is applied to a clear polyethylene terephthalate support (approximately 4 cm×4 cm) and spun at 4,000 RPM using the Spin Coating equipment, Model No. EC101, available from Headway Research, Inc., Garland, Tex. The transmission spectra of the so prepared dye samples are then recorded.

Preferred "NB couplers" form a dye which, in n-butyl sebacate, has a LBW of the absorption spectra upon "spin coating" which is at least 15 nm, preferably at least 25 nm, less than that of the same dye in a 3% solution (w/v) in acetonitrile.

In a preferred embodiment the cyan dye-forming "NB coupler" useful in the invention has the formula (IA)

(IA)

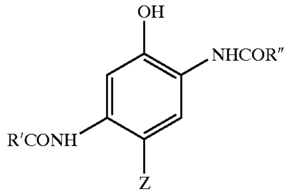

wherein

R' and R" are substituents selected such that the coupler is a "NB coupler", as herein defined, and Z is a hydrogen atom or a group, which can be split off by the reaction of the coupler with an oxidized color-developing agent.

The coupler of formula (IA) is a 2,5-diamido phenolic cyan coupler wherein the substituents R' and R" are preferably independently selected from unsubstituted or substituted alkyl, aryl, amino, alkoxy and heterocyclyl groups.

In a further preferred embodiment, the "NB coupler" has the formula (I):

(I)

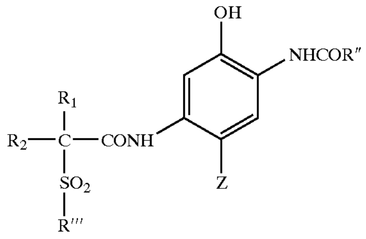

wherein

R" and R'" are independently selected from unsubstituted or substituted alkyl, aryl, amino, alkoxy and heterocyclyl groups and Z is as hereinbefore defined, $R_1$ and $R_2$ are independently hydrogen or an unsubstituted or substituted alkyl group, and Typically, R" is an alkyl, amino or aryl group, suitably a phenyl group. R'" is desirably an alkyl or aryl group or a 5–10 membered heterocyclic ring which contains one or more heteroatoms selected from nitrogen, oxygen and sulfur, which ring group is unsubstituted or substituted.

In the preferred embodiment the coupler of formula (I) is a 2,5-diamido phenol in which the 5-amido moiety is an amide of a carboxylic acid which is substituted in the alpha position by a particular sulfone (—$SO_2$—) group, such as, for example, described in U.S. Pat. No. 5,686,235. The sulfone moiety is an unsubstituted or substituted alkylsulfone or a heterocyclyl sulfone or it is an arylsulfone, which is preferably substituted, in particular in the meta and/or para position.

Couplers having these structures of formulae (I) or (IA) comprise cyan dye-forming "NB couplers" which form image dyes having very sharp-cutting dye hues on the short wavelength side of the absorption curves with absorption maxima ($\lambda_{max}$) which are shifted hypsochromically and are generally in the range of 620–645 nm, which is ideally suited for producing excellent color reproduction and high color saturation in color photographic papers.

Referring to formula (I), $R_1$ and $R_2$ are independently hydrogen or an unsubstituted or substituted alkyl group, preferably having from 1 to 24 carbon atoms and in particular 1 to 10 carbon atoms, suitably a methyl, ethyl, n-propyl, isopropyl, butyl or decyl group or an alkyl group substituted with one or more fluoro, chloro or bromo atoms, such as a trifluoromethyl group. Suitably, at least one of $R_1$ and $R_2$ is a hydrogen atom and if only one of $R_1$ and $R_2$ is a hydrogen atom then the other is preferably an alkyl group having 1 to 4 carbon atoms, more preferably one to three carbon atoms and desirably two carbon atoms.

As used herein and throughout the specification unless where specifically stated otherwise, the term "alkyl" refers to an unsaturated or saturated straight or branched chain alkyl group, including alkenyl, and includes aralkyl and cyclic alkyl groups, including cycloalkenyl, having 3–8 carbon atoms and the term 'aryl' includes specifically fused aryl.

In formula (I), R" is suitably an unsubstituted or substituted amino, alkyl or aryl group or a 5–10 membered heterocyclic ring which contains one or more heteroatoms selected from nitrogen, oxygen and sulfur, which ring is unsubstituted or substituted, but is more suitably an unsubstituted or substituted phenyl group.

Examples of suitable substituent groups for this aryl or heterocyclic ring include cyano, chloro, fluoro, bromo, iodo, alkyl- or aryl-carbonyl, alkyl- or aryl-oxycarbonyl, carbonamido, alkyl- or aryl-carbonamido, alkyl- or aryl-sulfonyl, alkyl- or aryl-sulfonyloxy, alkyl- or aryl-oxysulfonyl, alkyl- or aryl-sulfoxide, alkyl- or aryl-sulfamoyl, alkyl- or aryl-sulfonamido, aryl, alkyl, alkoxy, aryloxy, nitro, alkyl- or aryl-ureido and alkyl- or aryl-carbamoyl groups, any of which may be further substituted. Preferred groups are halogen, cyano, alkoxycarbonyl, alkylsulfamoyl, alkyl-sulfonamido, alkylsulfonyl, carbamoyl, alkylcarbamoyl or alkylcarbonamido. Suitably, R" is a 4-chlorophenyl, 3,4-di-chlorophenyl, 3,4-difluorophenyl, 4-cyanophenyl, 3-chloro-4-cyanophenyl, pentafluorophenyl, or a 3- or 4-sulfonamidophenyl group.

In formula (I), when R'" is alkyl it may be unsubstituted or substituted with a substituent such as halogen or alkoxy. When R'" is aryl or a heterocycle, it may be substituted. Desirably it is not substituted in the position alpha to the sulfonyl group.

In formula (I), when R'" is a phenyl group, it may be substituted in the meta and/or para positions with one to three substituents independently selected from the group consisting of halogen, and unsubstituted or substituted alkyl, alkoxy, aryloxy, acyloxy, acylamino, alkyl- or aryl-sulfonyloxy, alkyl- or aryl-sulfamoyl, alkyl- or aryl-sulfamoylamino, alkyl- or aryl-sulfonamido, alkyl- or aryl-ureido, alkyl- or aryl-oxycarbonyl, alkyl- or aryl-oxy-carbonylamino and alkyl- or aryl-carbamoyl groups.

In particular each substituent may be an alkyl group such as methyl, t-butyl, heptyl, dodecyl, pentadecyl, octadecyl or 1,1,2,2-tetramethylpropyl, an alkoxy group such as methoxy, t-butoxy, octyloxy, dodecyloxy, tetradecyloxy, hexadecyloxy or octadecyloxy, an aryloxy group such as phenoxy, 4-t-butylphenoxy or 4-dodecyl-phenoxy, an alkyl- or aryl-acyloxy group such as acetoxy or dodecanoyloxy, an alkyl- or aryl-acylamino group such as acetamido, hexadecanamido or benzamido, an alkyl- or aryl-sulfonyloxy group such as methyl-sulfonyloxy, dodecylsulfonyloxy or 4-methylphenyl-sulfonyloxy, an alkyl- or aryl-sulfamoyl-group such as N-butylsulfamoyl or N-4-t-butylphenylsulfamoyl, an alkyl- or aryl-sulfamoylamino group such as N-butyl-sulfamoylamino or N-4-t-butylphenylsulfamoyl-amino, an alkyl- or aryl-sulfonamido group such as methane-sulfonamido, hexadecanesulfonamido or 4-chlorophenyl-sulfonamido, an alkyl- or aryl-ureido group such as methylureido or phenylureido, an alkoxy- or aryloxy-carbonyl such as methoxycarbonyl or phenoxycarbonyl, an alkoxy- or aryloxy-carbonylamino group such as methoxy-carbonylamino or phenoxycarbonylamino, an alkyl- or aryl-carbamoyl group such as N-butylcarbamoyl or N-methyl-N-dodecylcarbamoyl, or a perfluoroalkyl group such as trifluoromethyl or heptafluoropropyl.

Suitably the above substituent groups have 1 to 30 carbon atoms, more preferably 8 to 20 aliphatic carbon atoms. A desirable substituent is an alkyl group of 12 to 18 aliphatic carbon atoms such as dodecyl, pentadecyl or octadecyl or an alkoxy group with 8 to 18 aliphatic carbon atoms such as dodecyloxy and hexadecyloxy or a halogen such as a meta or para chloro group, carboxy or sulfonamido. Any such groups may contain interrupting heteroatoms such as oxygen to form e.g. polyalkylene oxides.

In formula (I) or (IA) Z is a hydrogen atom or a group which can be split off by the reaction of the coupler with an oxidized color developing agent, known in the photographic art as a 'coup ling-off group' and may preferably be hydrogen, chloro, fluoro, substituted aryloxy or mercaptotetrazole, more preferably hydrogen or chloro.

The presence or absence of such groups determines the chemical equivalency of the coupler, i.e., whether it is a 2-equivalent or 4-equivalent coupler, and its particular identity can modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction, and the like.

Representative classes of such coupling-off groups include, for example, halogen, alkoxy, aryloxy, heterocyclyloxy, sulfonyloxy, acyloxy, acyl, heterocyclylsulfonamido, heterocyclylthio, benzothiazolyl, phosophonyloxy, alkylthio, arylthio, and arylazo. These coupling-off groups are described in the art, for example, in U.S. Pat. Nos. 2,455,169, 3,227,551, 3,432,521, 3,467,563, 3,617,291, 3,880,661, 4,052,212, and 4,134,766, and in U.K. Patent Nos. and published applications 1,466,728, 1,531,927, 1,533,039, 2,066,755A, and 2,017,704A. Halogen, alkoxy, and aryloxy groups are most suitable.

Examples of specific coupling-off groups are —Cl, —F, —Br, —SCN, $—OCH_3$, $—OC_6H_5$, $—OCH_2C(=O)NHCH_2CH_2OH$, $—OCH_2C(O)NHCH_2CH_2OCH_3$, $—OCH_2C(O)NHCH_2CH_2OC(=O)OCH_3$, $—P(=O)(OC_2H_5)_2$, $—SCH_2CH_2COOH$,

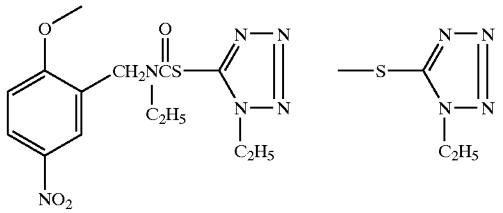

-continued

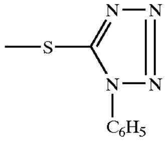

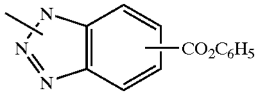

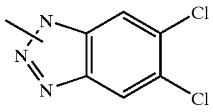

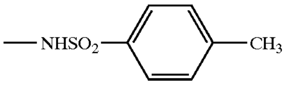

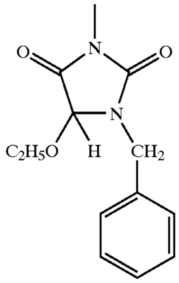

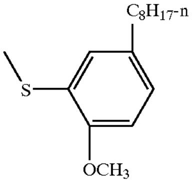

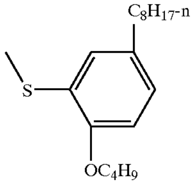

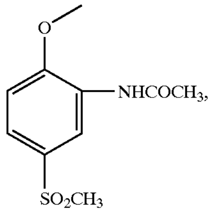

and

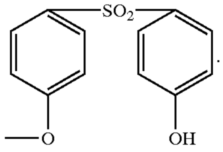

Typically, the coupling-off group is a chlorine atom, hydrogen atom or p-methoxyphenoxy group.

It is essential that the substituent groups be selected so as to adequately ballast the coupler and the resulting dye in the organic solvent in which the coupler is dispersed. The ballasting may be accomplished by providing hydrophobic substituent groups in one or more of the substituent groups. Generally a ballast group is an organic radical of such size and configuration as to confer on the coupler molecule sufficient bulk and aqueous insolubility as to render the coupler substantially nondiffusible from the layer in which it is coated in a photographic element. Thus the combination of substituent are suitably chosen to meet these criteria. To be effective, the ballast will usually contain at least 8 carbon atoms and typically contains 10 to 30 carbon atoms. Suitable ballasting may also be accomplished by providing a plurality of groups, which in combination meet these criteria. $R_1$ in formula (I) is a small alkyl group or hydrogen. Therefore, in these embodiments the ballast would be primarily located as part of the other groups. Furthermore, even if the coupling-off group Z contains a ballast it is often necessary to ballast the other substituents as well, since Z is eliminated from the molecule upon coupling, thus, the ballast is most advantageously provided as part of groups other than Z.

The following examples further illustrate preferred coupler. It is not to be construed that the present invention is limited to these examples.

IC-1

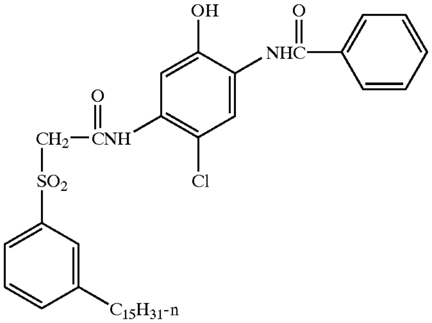

IC-2

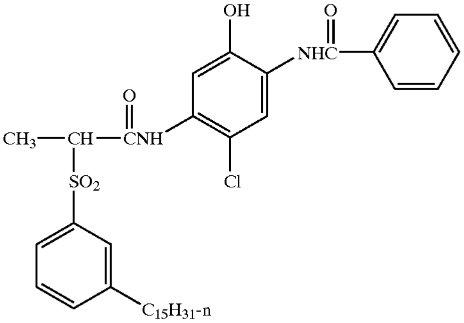

IC-3

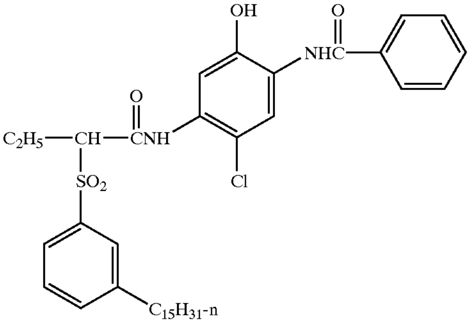

IC-4

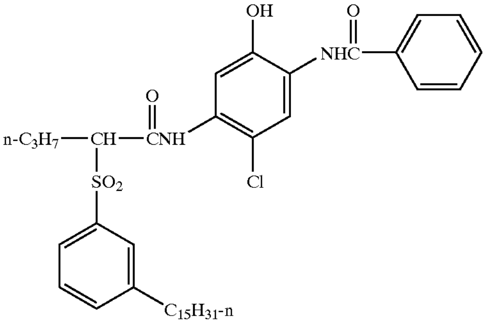

-continued
IC-5
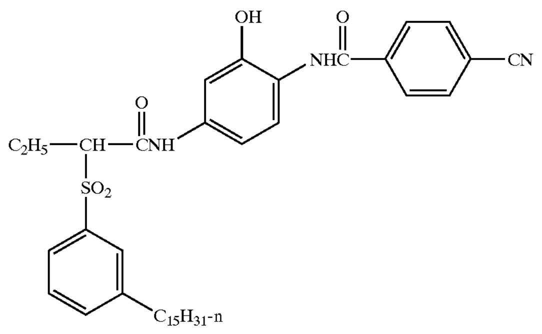
IC-6
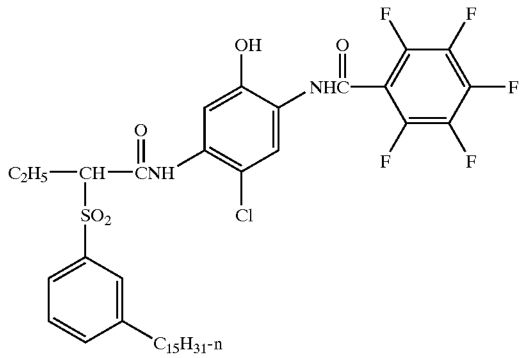
IC-7
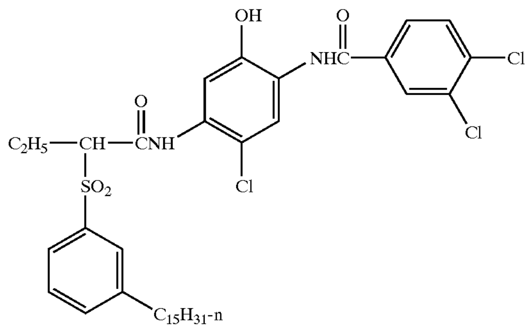
IC-8
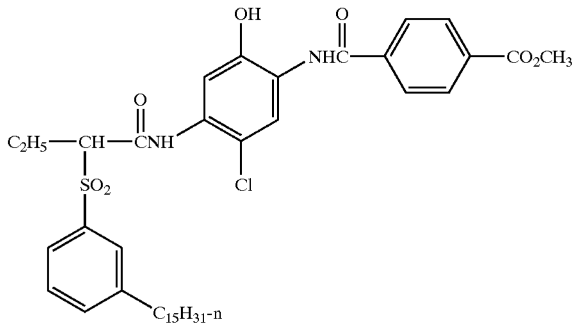
-continued
IC-9
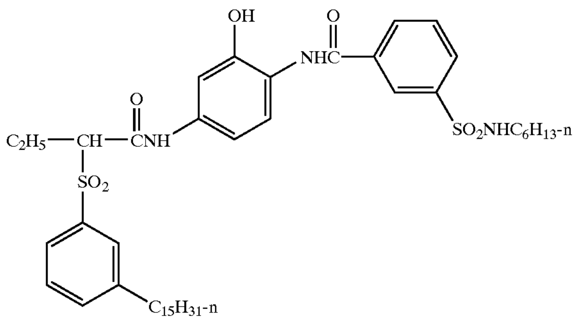
IC-10
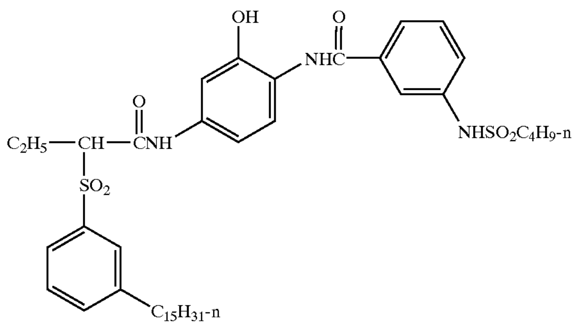
IC-11
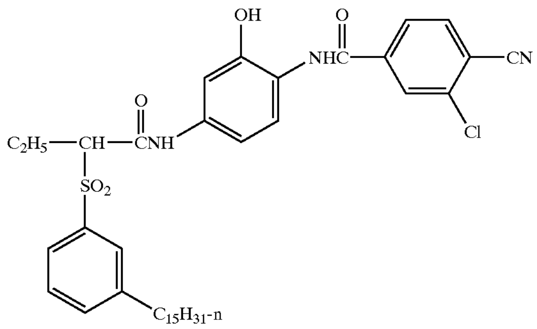
IC-12
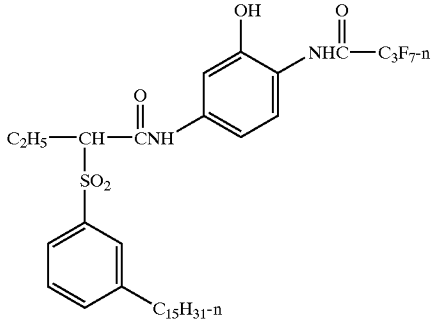

-continued
IC-13
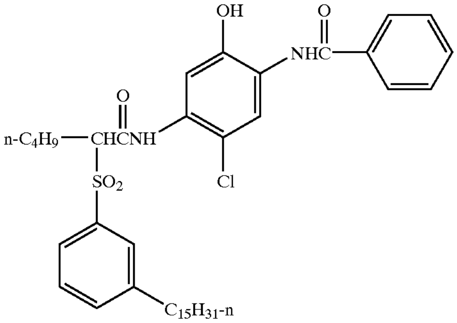
IC-14
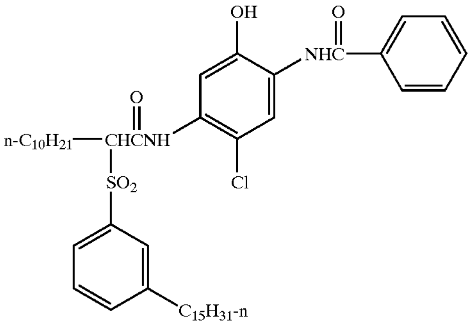
IC-15
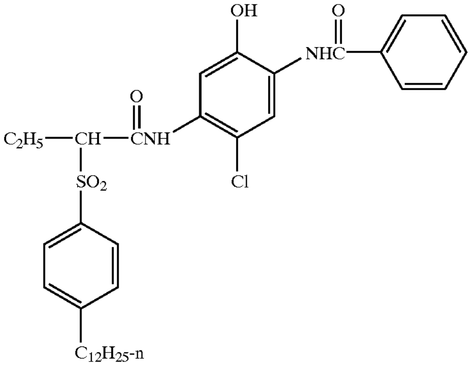
IC-16
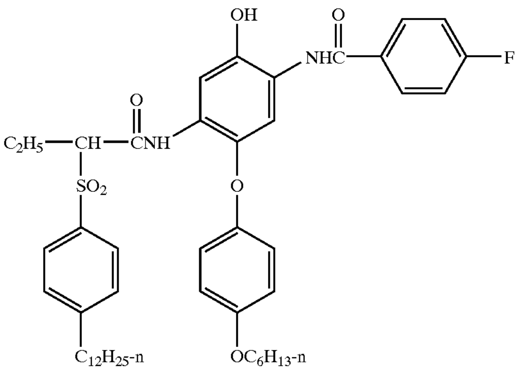
-continued
IC-17
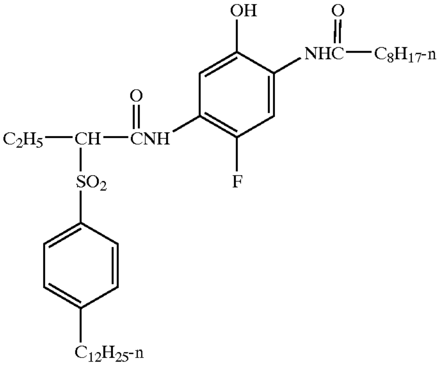
IC-18
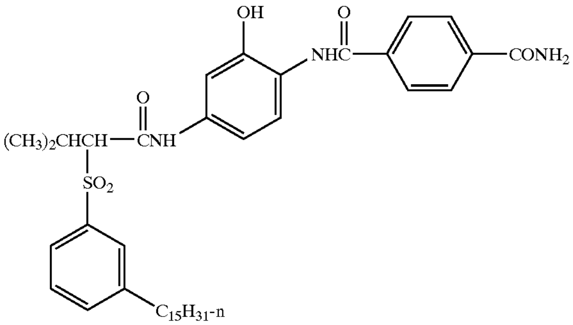
IC-19
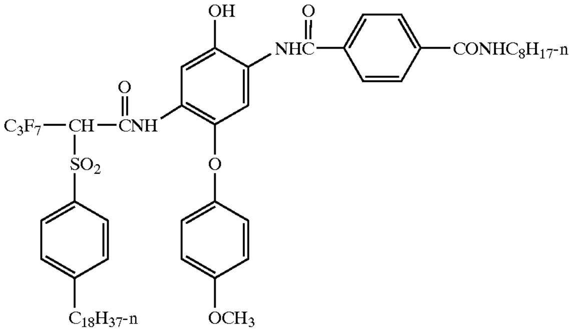
IC-20
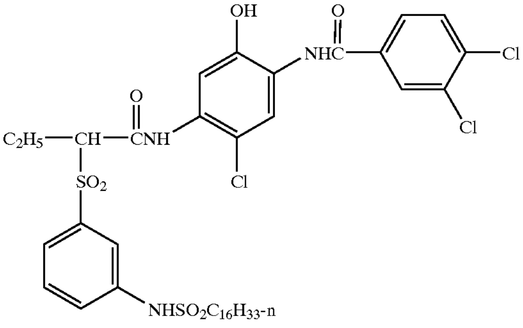

-continued
IC-21
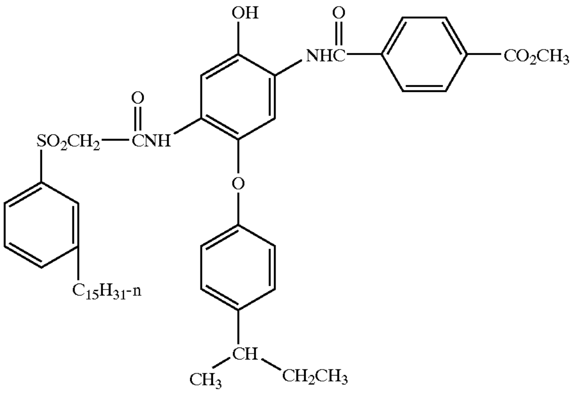
IC-22
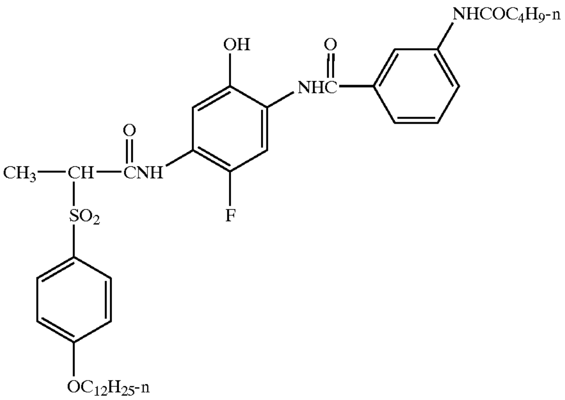
IC-23
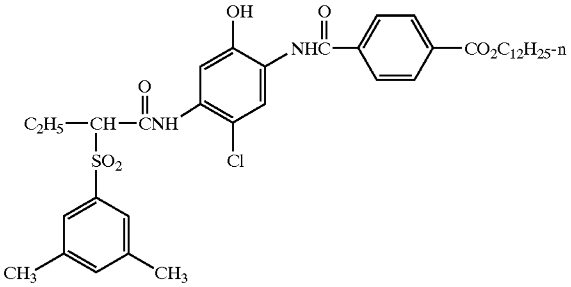
IC-24
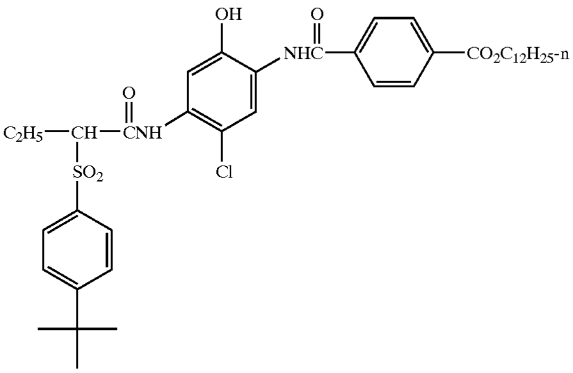
-continued
IC-25
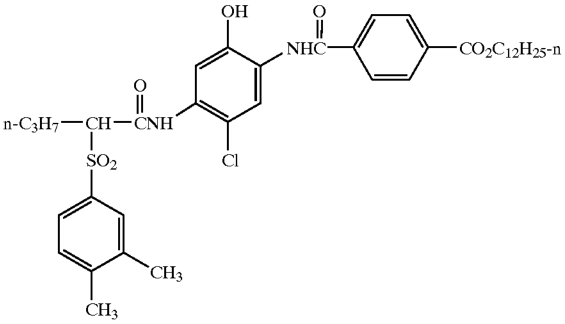
IC-26
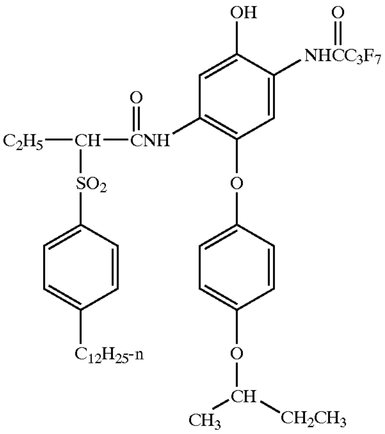
IC-27
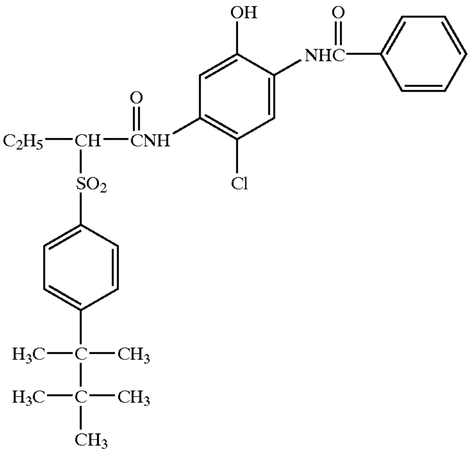
IC-28
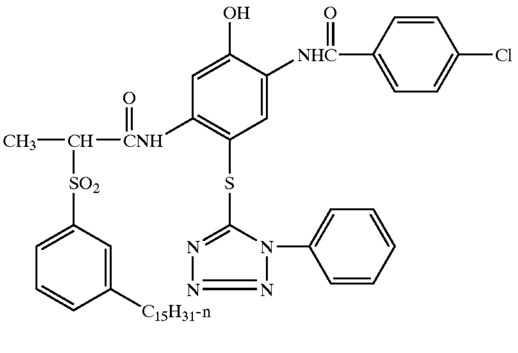

-continued
IC-29
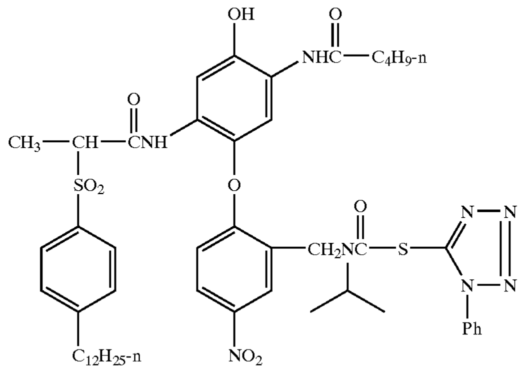
IC-30
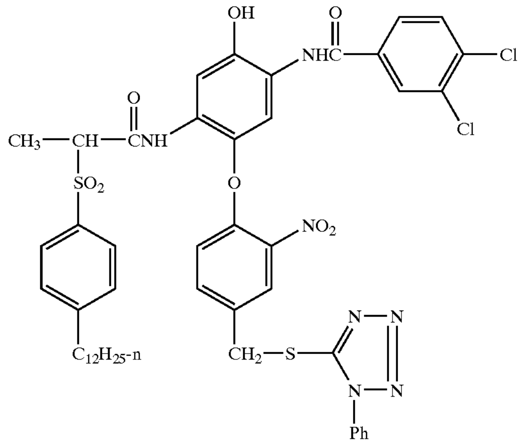
IC-31
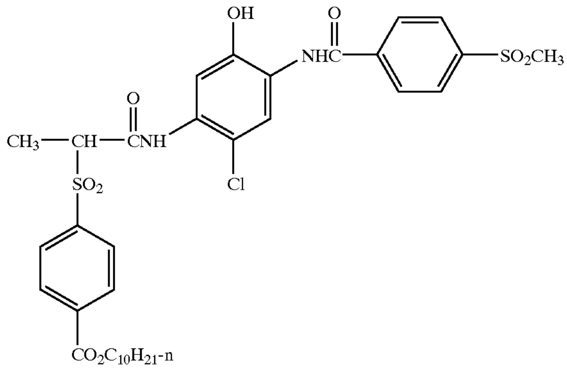
IC-32
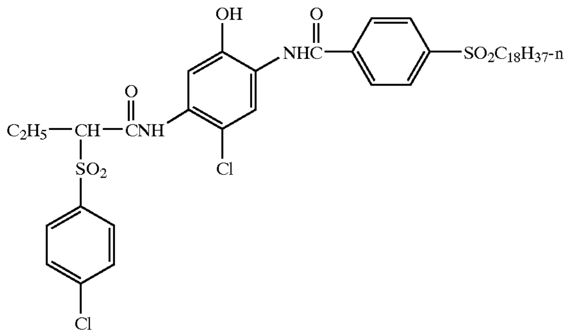
-continued
IC-33
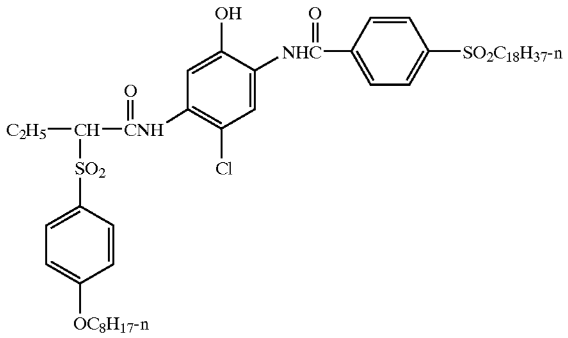
IC-34
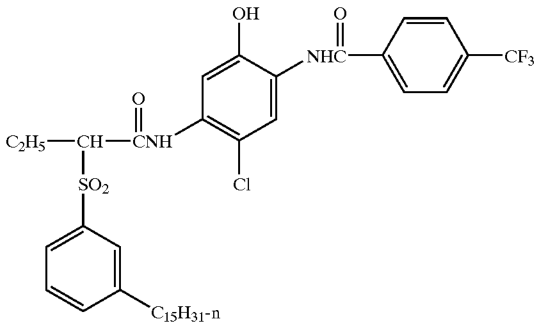
IC-35
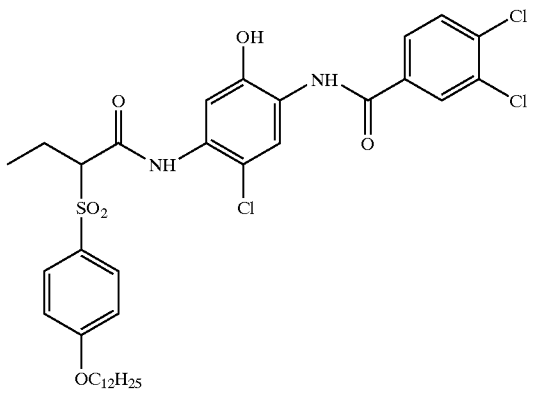
IC-36
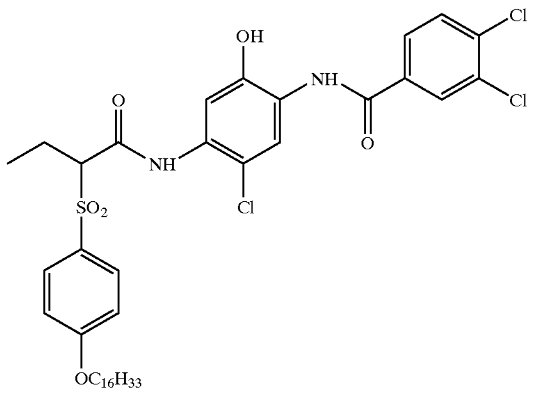

-continued

IC-37

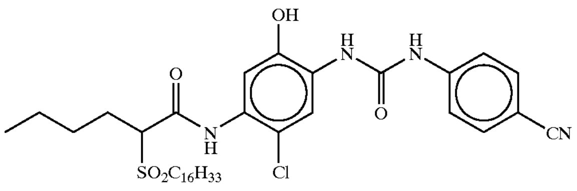

IC-38

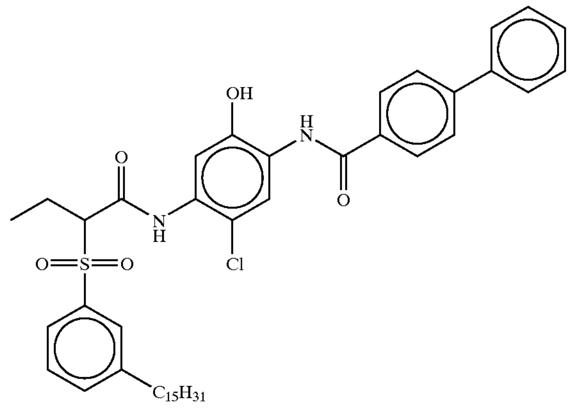

IC-39

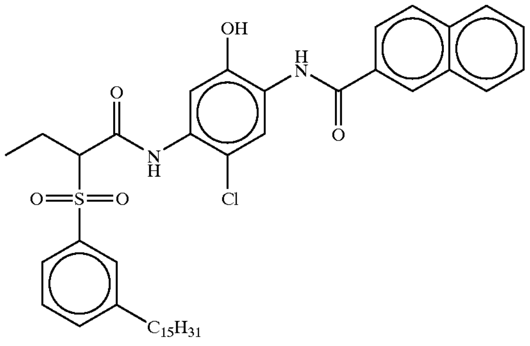

IC-40

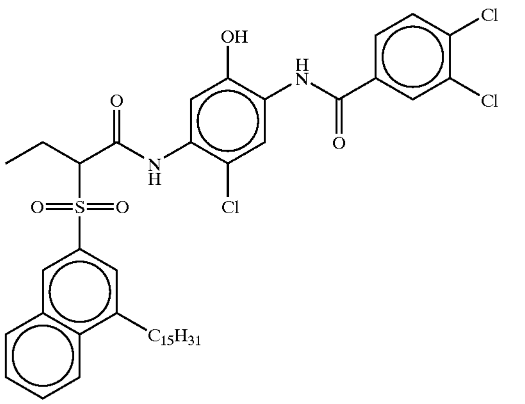

Preferred couplers are IC-3, IC-7, IC-35, and IC-36 because of their suitably narrow left bandwidths.

Couplers that form magenta dyes upon reaction with oxidized color developing agent are described in such representative patents and publications as: U.S. Pat. Nos. 2,311,082, 2,343,703, 2,369,489, 2,600,788, 2,908,573, 3,062,653, 3,152,896, 3,519,429, 3,758,309, and "Farbkuppler-eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents. Especially preferred couplers are 1H-pyrazolo [5,1-c]-1,2,4-triazole and 1H-pyrazolo [1,5-b]-1,2,4-triazole. Examples of 1H-pyrazolo [5,1-c]-1,2,4-triazole couplers are described in U.K. Patent Nos. 1,247,493, 1,252,418, 1,398,979, U.S. Pat. Nos. 4,443,536, 4,514,490, 4,540,654, 4,590,153, 4,665,015, 4,822,730, 4,945,034, 5,017,465, and 5,023,170. Examples of 1H-pyrazolo [1,5-b]-1,2,4-triazoles can be found in European Patent applications 176,804, 177,765, U.S. Pat. Nos. 4,659,652, 5,066,575, and 5,250,400.

Typical pyrazoloazole and pyrazolone couplers are represented by the following formulas:

MAGENTA-1

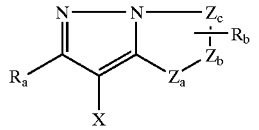

MAGENTA-2

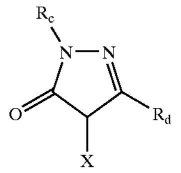

wherein $R_a$ and $R_b$ independently represent H or a substituent, $R_c$ is a substituent (preferably an aryl group), $R_d$ is a substituent (preferably an anilino, carbonamido, ureido, carbamoyl, alkoxy, aryloxycarbonyl, alkoxycarbonyl, or N-heterocyclic group), X is hydrogen or a coupling-off group, and $Z_a$, $Z_b$, and $Z_c$ are independently a substituted methine group, =N—, =C—, or —NH—, provided that one of either the $Z_a$—$Z_b$ bond or the $Z_b$—$Z_c$ bond is a double bond and the other is a single bond, and when the $Z_b$—$Z_c$ bond is a carbon-carbon double bond, it may form part of an aromatic ring, and at least one of $Z_a$, $Z_b$, and $Z_c$ represents a methine group connected to the group $R_b$.

Specific examples of such couplers are:

M-1

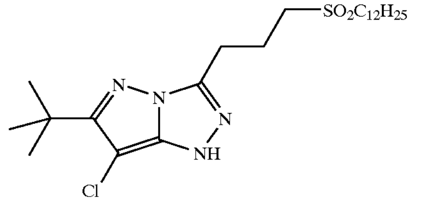

M-2

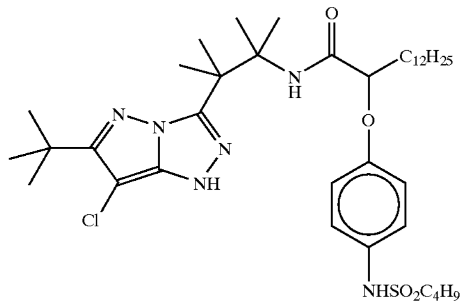

-continued

M-3

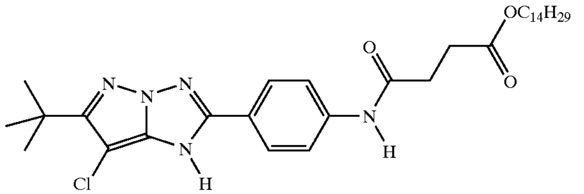

M-4

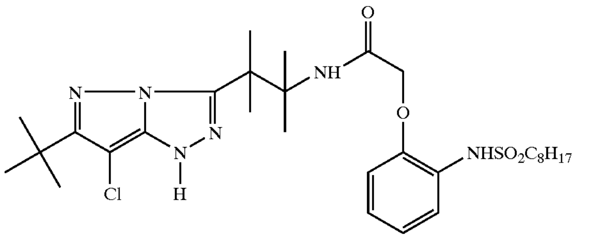

M-5

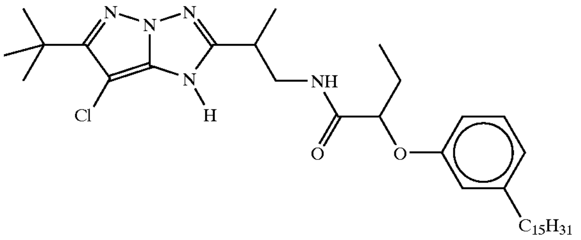

Couplers that form yellow dyes upon reaction with oxidized color developing agent are described in such representative patents and publications as: U.S. Pat. Nos. 2,298,443, 2,407,210, 2,875,057, 3,048,194, 3,265,506, 3,447,928, 3,960,570, 4,022,620, 4,443,536, 4,910,126, and 5,340,703 and "Farbkuppler-eine Literature Ubersicht," published in Agfa Mitteilungen, Band III, pp. 112–126 (1961). Such couplers are typically open chain ketomethylene compounds. Also preferred are yellow couplers such as described in, for example, European Patent Application Nos. 482,552, 510, 535, 524, 540, 543,367, and U.S. Pat. No. 5,238,803. For improved color reproduction, couplers which give yellow dyes that cut off sharply on the long wavelength side are particularly preferred (for example, see U.S. Pat. No. 5,360,713).

Typical preferred yellow couplers are represented by the following formulas:

YELLOW-1

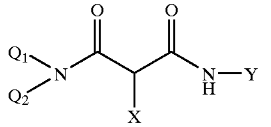

YELLOW-2

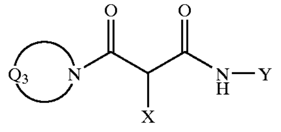

-continued

YELLOW-3

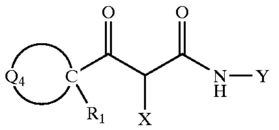

YELLOW-4

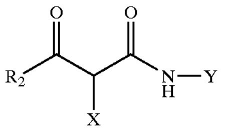

wherein $R_1$, $R_2$, $Q_1$ and $Q_2$ each represents a substituent, X is hydrogen or a coupling-off group, Y represents an aryl group or a heterocyclic group, $Q_3$ represents an organic residue required to form a nitrogen-containing heterocyclic group together with the >N—, and $Q_4$ represents nonmetallic atoms necessary to from a 3- to 5-membered hydrocarbon ring or a 3- to 5-membered heterocyclic ring which contains at least one hetero atom selected from N, O, S, and P in the ring. Particularly preferred is when $Q_1$ and $Q_2$ each represent an alkyl group, an aryl group, or a heterocyclic group, and $R_2$ represents an aryl or tertiary alkyl group.

Preferred yellow couplers can be of the following general structures:

Y-1

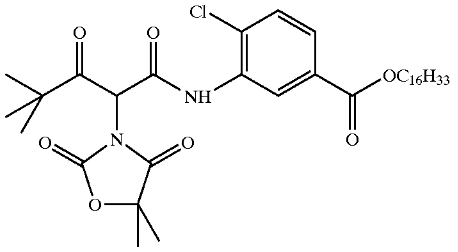

Y-2

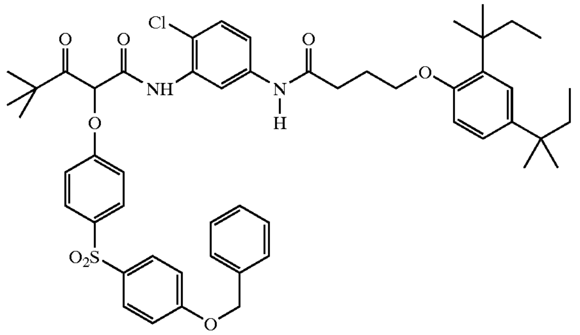

Y-3

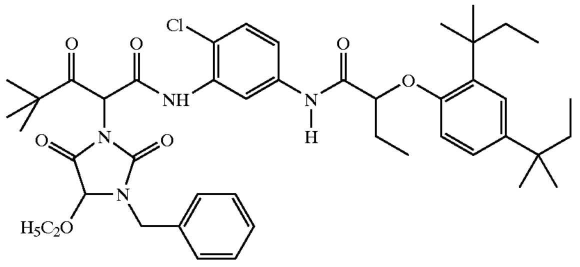

-continued

Y-4

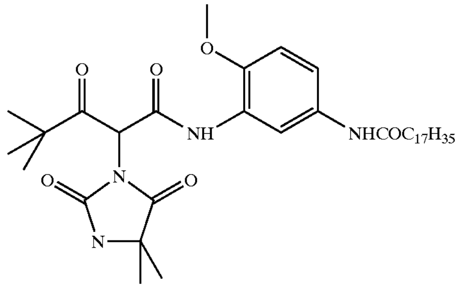

Y-5

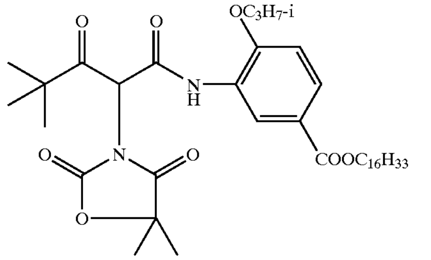

Y-6

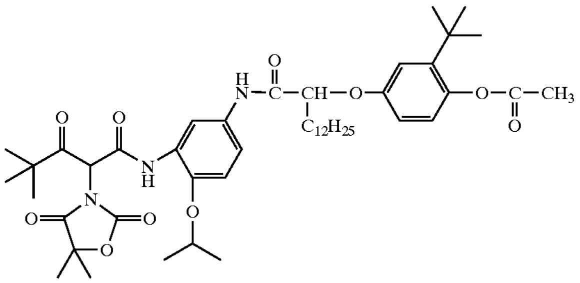

Unless otherwise specifically stated, substituent groups, which may be substituted, on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine, nitro, hydroxyl, cyano, carboxyl, or groups which may be further substituted, such as alkyl, including straight or branched chain alkyl, such as methyl, trifluoromethyl, ethyl, t-butyl, 3-(2,4-di-t-pentylphenoxy) propyl, and tetradecyl, alkenyl, such as ethylene, 2-butene, alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy, aryl such as phenyl, 4-t-butylphenyl, 2,4,6-trimethylphenyl, naphthyl, aryloxy, such as phenoxy, 2-methylphenoxy, alpha- or beta-naphthyloxy, and 4-tolyloxy, carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido, sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido, sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl, carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl, acyl, such as acetyl, (2,4-di-t-amylphenoxy)acetyl, phenoxycarbonyl, p-dodecyloxyphenoxycarbonyl, methoxycarbonyl, butoxycarbonyl, tetradecyloxycarbonyl, ethoxycarbonyl, benzyloxycarbonyl, 3-pentadecyloxycarbonyl, and dodecyloxycarbonyl, sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl, sulfonyloxy, such as dodecylsulfonyloxy, and hexadecylsulfonyloxy, sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, andp-toluylsulfinyl, thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio, acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy, amino, such as phenylanilino, 2-chloroanilino, diethylamino, dodecylamino, imino, such as 1 (N-phenylimido)ethyl, N-succinimido or 3-benzylhydantoinyl, phosphate, such as dimethylphosphate and ethylbutylphosphate, phosphite, such as diethyl and dihexylphosphite, a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl, quaternary ammonium, such as triethylammonium, and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups. Generally, the above groups and substituents thereof may include those having up to 48 carbon atoms, typically 1 to 36 carbon atoms and usually less than 24 carbon atoms, but greater numbers are possible depending on the particular substituents selected.

Representative substituents on ballast groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

Stabilizers and scavengers that can be used in these photographic elements, but are not limited to, the following.

ST-1

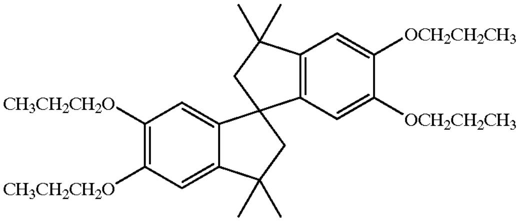

ST-2

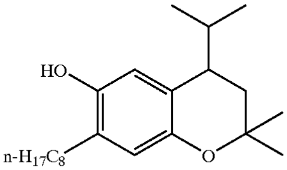

ST-3

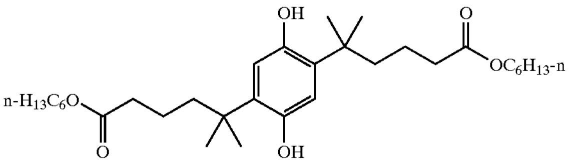

ST-4

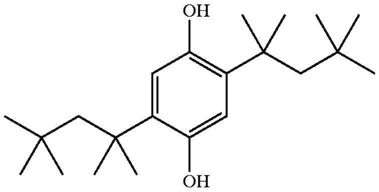

ST-5

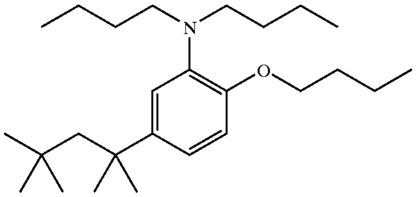

ST-6

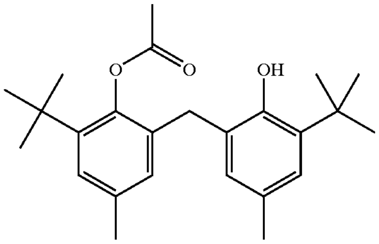

-continued

ST-7

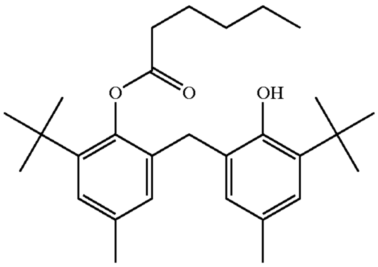

ST-8

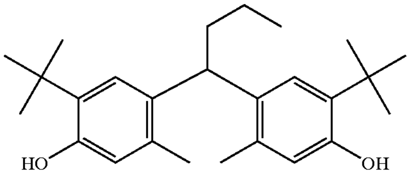

ST-9

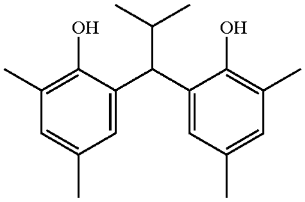

ST-10

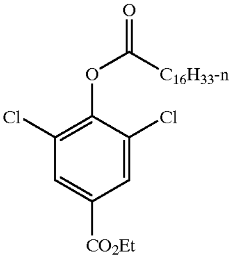

ST-11

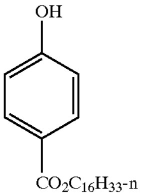

ST-12

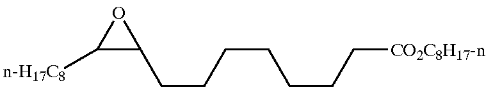

ST-13

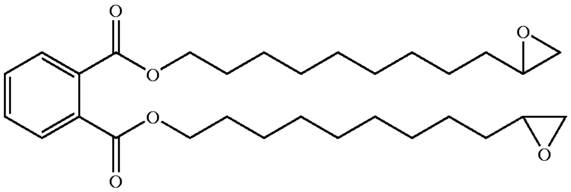

-continued

ST-14

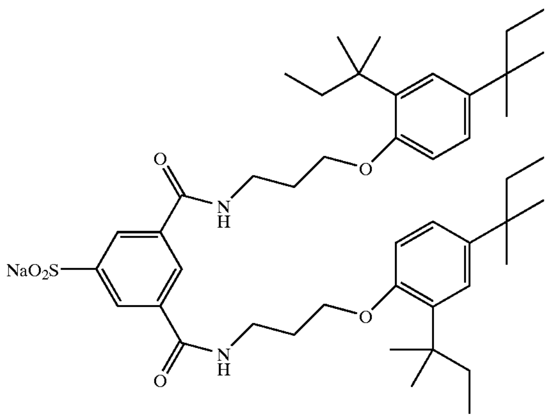

ST-15

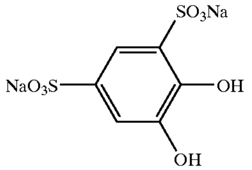

ST-16

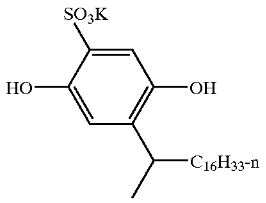

ST-17

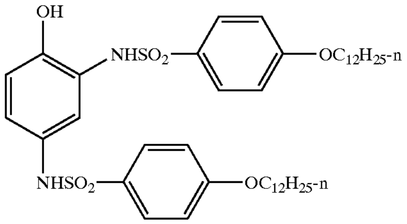

ST-18

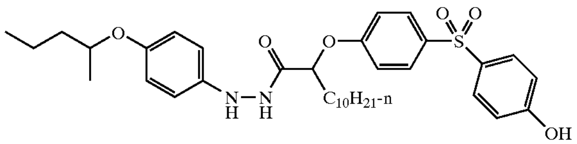

ST-19

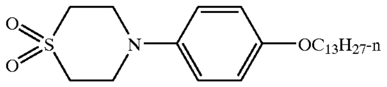

ST-20

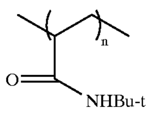

n = 75–8,000

ST-21

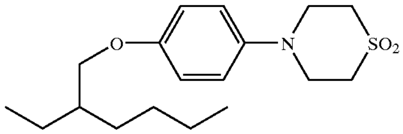

-continued

ST-22

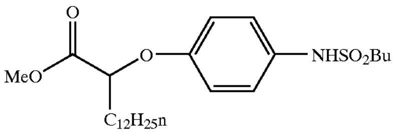

ST-23

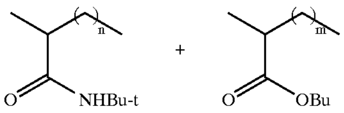

n:m 1:1 mw = 75–100,000

ST-24

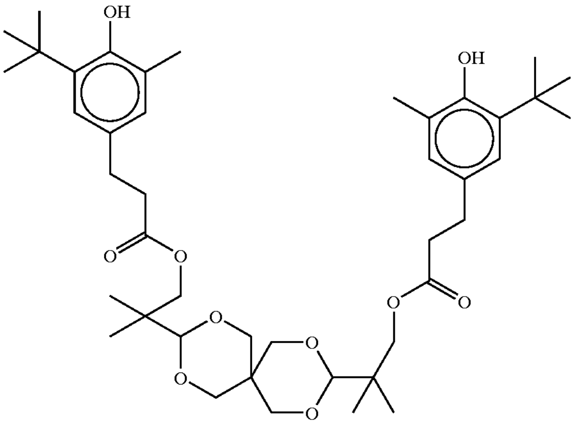

Examples of solvents, which may be used in the invention, include the following:

| | |
|---|---|
| Tritolyl phosphate | S-1 |
| Dibutyl phthalate | S-2 |
| Diundecyl phthalate | S-3 |
| N,N-Diethyldodecanamide | S-4 |
| N,N-Dibutyldodecanamide | S-5 |
| Tris(2-ethylhexyl)phosphate | S-6 |
| Acetyl tributyl citrate | S-7 |
| 2,4-Di-tert-pentylphenol | S-8 |
| 2-(2-Butoxyethoxy)ethyl acetate | S-9 |
| 1,4-Cyclohexyldimethylene bis(2-ethylhexanoate) | S-10 |
| Tributyl citrate | S-11 |
| Dibutyl sebacate | S-12 |
| Oleyl Alcohol | S-13 |

The dispersions used in photographic elements may also include ultraviolet (UV) stabilizers and so called liquid UV stabilizers such as described in U.S. Pat. Nos. 4,992,358, 4,975,360, and 4,587,346. Examples of UV stabilizers are shown below.

UV-1

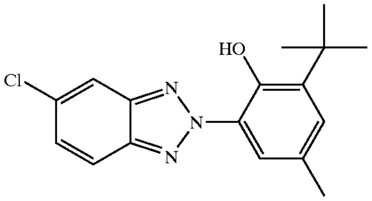

-continued

UV-2

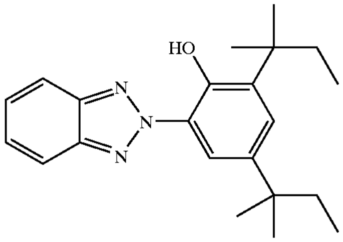

UV-3

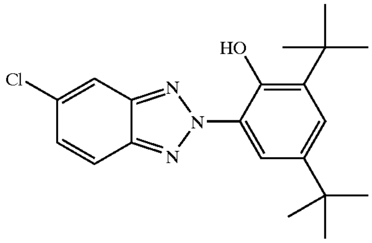

UV-4

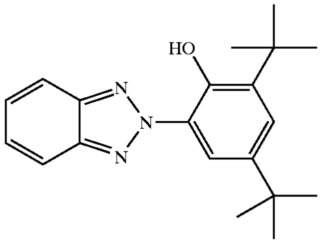

UV-5

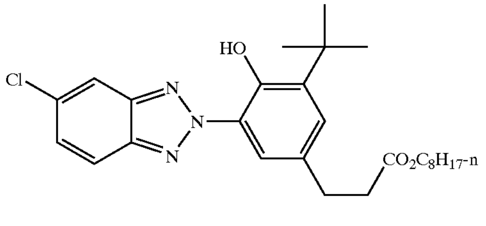

UV-6

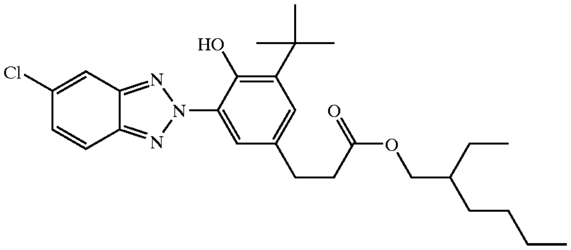

UV-7

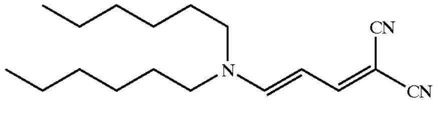

UV-8

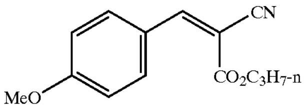

The aqueous phase of the photographic dispersions may include surfactants. Surfactant may be cationic, anionic, zwitterionic or non-ionic. Useful surfactants include, but are not limited to, the following:

SF-1

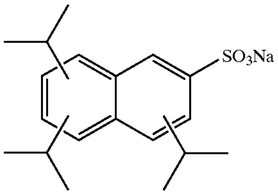

SF-2

$CF_3 \bullet (CF_2)_7 \bullet SO_3Na$

SF-3

$CH_3 \bullet (CH_2)_n \bullet SO_3Na$, n = 12–14

SF-4

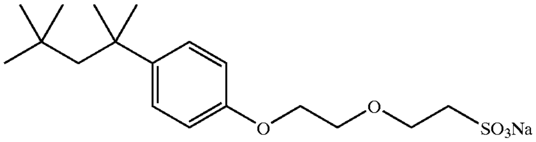

SF-5

$CH_3 \bullet (CH_2)_{11} \bullet OSO_3Na$

SF-6

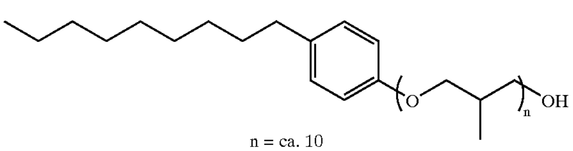

n = ca. 10

SF-7

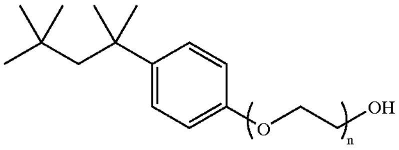

n = ca. 40

SF-8

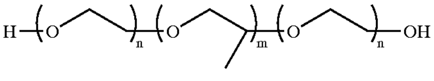

n = ca. 6, m = ca. 2

SF-9

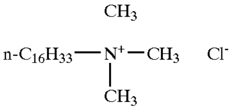

SF-10

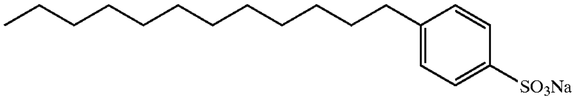

SF-11

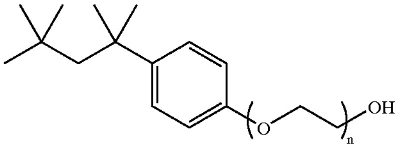

n = ca. 10

SF-12

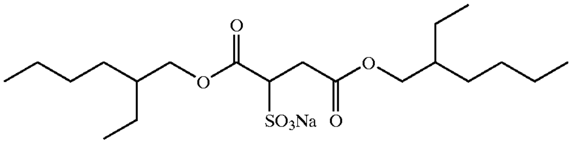

-continued

SF-13

Mixture of $F_3C—(CF_2)_5—CH_2—CH_2—SO_3H$ and $F_3C—(CF_2)_5—CH_2—CH_2—SO_3H$ $\cdot NH_3$ Further, it is contemplated to stabilize photographic dispersions prone to particle growth through the use of hydrophobic, photographically inert compounds such as disclosed by Zengerle et al in U.S. Pat. No. 5,468,604.

In a preferred embodiment the invention employs recording elements which are constructed to contain at least three silver halide emulsion layer units. A preferred element may additionally comprise a UV layer and/or an overcoat layer above the red-sensitized layer. A suitable full color, multilayer format for a recording element used in the invention is represented by Structure I.

| STRUCTURE I |
|---|
| Red-sensitized |
| cyan dye image-forming silver halide emulsion unit |
| Interlayer |
| Green-sensitized |
| magenta dye image-forming silver halide emulsion unit |
| Interlayer |
| Blue-sensitized |
| yellow dye image-forming silver halide emulsion unit |
| ///// Support ///// |

wherein the red-sensitized, cyan dye image-forming silver halide emulsion unit is situated nearest the support, next in order is the green-sensitized, magenta dye image-forming unit, followed by the uppermost blue-sensitized, yellow dye image-forming unit. The image-forming units are separated from each other by hydrophilic colloid interlayers containing an oxidized developing agent scavenger to prevent color contamination. Silver halide emulsions satisfying the grain and gelatino-peptizer requirements described above can be present in any one or combination of the emulsion layer units. Additional useful multicolor, multilayer formats for an element of the invention include structures as described in U.S. Pat. No. 5,783,373. Each of such structures preferably would contain at least three silver halide emulsions comprised of high chloride grains having at least 50 percent of their surface area bounded by {100} crystal faces and containing dopants from classes (i) and (ii), as described above. Preferably each of the emulsion layer units contains emulsion satisfying these criteria.

Conventional features that can be incorporated into multilayer (and particularly multicolor) recording elements contemplated for use are illustrated by *Research Disclosure,* Item 38957, cited above:

XI. Layers and layer arrangements

XII. Features applicable only to color negative

XIII. Features applicable only to color positive

B. Color reversal

C. Color positives derived from color negatives

XIV. Scan facilitating features.

Layers of imaging elements other than the image-forming layer are commonly referred to as auxiliary layers. There are many different types of auxiliary layers such as, for example, subbing layers, backing layers, interlayers, overcoat layers, receiving layers, stripping layers, antistatic layers, transparent magnetic layers, and the like.

The recording elements comprising the radiation sensitive high chloride emulsion layers according to this invention can be conventionally optically printed, or in accordance with a particular embodiment of the invention can be image-wise exposed in a pixel-by-pixel mode using suitable high energy radiation sources typically employed in electronic printing methods. Suitable actinic forms of energy encompass the ultraviolet, visible and infrared regions of the electromagnetic spectrum as well as electron-beam radiation and is conveniently supplied by beams from one or more light emitting diodes or lasers, including gaseous or solid state lasers. Exposures can be monochromatic, orthochromatic or panchromatic. For example, when the recording element is a multilayer multicolor element, exposure can be provided by laser or light emitting diode beams of appropriate spectral radiation, for example, infrared, red, green or blue wavelengths, to which such element is sensitive. Multicolor elements can be employed which produce cyan, magenta and yellow dyes as a function of exposure in separate portions of the electromagnetic spectrum, including at least two portions of the infrared region, as disclosed in the previously mentioned U.S. Pat. No. 4,619,892. Suitable exposures include those up to 2000 nm, preferably up to 1500 nm. Suitable light emitting diodes and commercially available laser sources are known and commercially available. Imagewise exposures at ambient, elevated or reduced temperatures and/or pressures can be employed within the useful response range of the recording element determined by conventional sensitometric techniques, as illustrated by T. H. James, *The Theory of the Photographic Process,* 4th Ed., Macmillan, 1977, Chapters 4, 6, 17, 18 and 23.

It has been observed that anionic $[MX_xY_yL_z]$ hexacoordination complexes, where M is a group 8 or 9 metal (preferably iron, ruthenium or iridium), X is halide or pseudohalide (preferably Cl, Br or CN) x is 3 to 5, Y is $H_2O$, y is 0 or 1, L is a C—C, H—C or C—N—H organic ligand, and Z is 1 or 2, are surprisingly effective in reducing high intensity reciprocity failure (HIRF), low intensity reciprocity failure (LIRF) and thermal sensitivity variance and in improving latent image keeping (LIK). As herein employed HIRF is a measure of the variance of photographic properties for equal exposures, but with exposure times ranging from $10^{-1}$ to $10^{-6}$ second. LIRF is a measure of the variance of photographic properties for equal exposures, but with exposure times ranging from $10^{-1}$ to 100 seconds. Although these advantages can be generally compatible with face centered cubic lattice grain structures, the most striking improvements have been observed in high (>50 mole %, preferably ≧90 mole %) chloride emulsions. Preferred C—C, H—C or C—N—H organic ligands are aromatic heterocycles of the type described in U.S. Pat. No. 5,462,849. The most effective C—C, H—C or C—N—H organic ligands are azoles and azines, either unsubstituted or containing alkyl, alkoxy or halide substituents, where the alkyl moieties contain from 1 to 8 carbon atoms. Particularly preferred azoles and azines include thiazoles, thiazolines and pyrazines.

The quantity or level of high energy actinic radiation provided to the recording medium by the exposure source is generally at least $10^{-4}$ ergs/cm$^2$, typically in the range of about $10^{-4}$ ergs/cm$^2$ to $10^{-3}$ ergs/cm$^2$ and often from $10^{-3}$ ergs/cm$^2$ to $10^2$ ergs/cm$^2$. Exposure of the recording element in a pixel-by-pixel mode as known in the prior art persists for only a very short duration or time. Typical maximum exposure times are up to 100$\mu$ seconds, often up to 10$\mu$ seconds, and frequently up to only 0.5$\mu$ seconds. Single or multiple exposures of each pixel are contemplated. The pixel density is subject to wide variation, as is obvious to those skilled in the art. The higher the pixel density, the sharper the images can be, but at the expense of equipment complexity. In general, pixel densities used in conventional electronic printing methods of the type described herein do not exceed $10^7$ pixels/cm$^2$ and are typically in the range of about $10^4$ to $10^6$ pixels/cm$^2$. An assessment of the technology of high-quality, continuous-tone, color electronic printing using silver halide photographic paper which discusses various features and components of the system, including exposure source, exposure time, exposure level and pixel density and other recording element characteristics is provided in Firth et al., *A Continuous-Tone Laser Color Printer*, Journal of Imaging Technology, Vol. 14, No. 3, June 1988, which is hereby incorporated herein by reference. As previously indicated herein, a description of some of the details of conventional electronic printing methods comprising scanning a recording element with high energy beams such as light emitting diodes or laser beams, are set forth in Hioki U.S. Pat. No. 5,126,235, European Patent Applications 479 167 A1 and 502 508 A1.

Once imagewise exposed, the recording elements can be processed in any convenient conventional manner to obtain a viewable image. Such processing is illustrated by *Research Disclosure*, Item 38957, cited above:

XVIII. Chemical development systems

XIX. Development

XX. Desilvering, washing, rinsing and stabilizing

In addition, a useful developer for the inventive material is a homogeneous, single part developing agent. The homogeneous, single-part color developing concentrate is prepared using a critical sequence of steps:

In the first step, an aqueous solution of a suitable color-developing agent is prepared. This color-developing agent is generally in the form of a sulfate salt. Other components of the solution can include an antioxidant for the color developing agent, a suitable number of alkali metal ions (in an at least stoichiometric proportion to the sulfate ions) provided by an alkali metal base, and a photographically inactive water-miscible or water-soluble hydroxy-containing organic solvent. This solvent is present in the final concentrate at a concentration such that the weight ratio of water to the organic solvent is from about 15:85 to about 50:50.

In this environment, especially at high alkalinity, alkali metal ions and sulfate ions form a sulfate salt that is precipitated in the presence of the hydroxy-containing organic solvent. The precipitated sulfate salt can then be readily removed using any suitable liquid/solid phase separation technique (including filtration, centrifugation or decantation). If the antioxidant is a liquid organic compound, two phases may be formed and the precipitate may be removed by discarding the aqueous phase.

The color developing concentrates include one or more color developing agents that are well known in the art that, in oxidized form, will react with dye forming color couplers in the processed materials. Such color developing agents include, but are not limited to, aminophenols, p-phenylenediamines (especially N,N-dialkyl-p-phenylenediamines) and others which are well known in the art, such as EP 0 434 097 A1 (published Jun. 26, 1991) and EP 0 530 921 A1 (published Mar. 10, 1993). It may be useful for the color developing agents to have one or more water-solubilizing groups as are known in the art. Further details of such materials are provided in *Research Disclosure*, publication 38957, pages 592–639 (September 1996). *Research Disclosure* is a publication of Kenneth Mason Publications Ltd., Dudley House, 12 North Street, Emsworth, Hampshire PO10 7DQ England (also available from Emsworth Design Inc., 121 West 19th Street, New York, N.Y. 10011). This reference will be referred to hereinafter as "*Research Disclosure*".

Preferred color developing agents include, but are not limited to, N,N-diethyl p-phenylenediamine sulfate (KODAK Color Developing Agent CD-2), 4-amino-3-methyl-N-(2-methane sulfonamidoethyl)aniline sulfate, 4-(N-ethyl-N-β-hydroxyethylamino)-2-methylaniline sulfate (KODAK Color Developing Agent CD-4), p-hydroxyethylethylaminoaniline sulfate, 4-(N-ethyl-N-2-methanesulfonylaminoethyl)-2-methylphenylenediamine sesquisulfate (KODAK Color Developing Agent CD-3), 4-(N-ethyl-N-2-methanesulfonylaminoethyl)-2-methylphenylenediamine sesquisulfate, and others readily apparent to one skilled in the art.

In order to protect the color developing agents from oxidation, one or more antioxidants are generally included in the color developing compositions. Either inorganic or organic antioxidants can be used. Many classes of useful antioxidants are known, including but not limited to, sulfites (such as sodium sulfite, potassium sulfite, sodium bisulfite and potassium metabisulfite), hydroxylamine (and derivatives thereof), hydrazines, hydrazides, amino acids, ascorbic acid (and derivatives thereof), hydroxamic acids, aminoketones, mono- and polysaccharides, mono- and polyamines, quaternary ammonium salts, nitroxy radicals, alcohols, and oximes. Also useful as antioxidants are 1,4-cyclohexadiones. Mixtures of compounds from the same or different classes of antioxidants can also be used if desired.

Especially useful antioxidants are hydroxylamine derivatives as described, for example, in U.S. Pat. Nos. 4,892,804, 4,876,174, 5,354,646, and 5,660,974, all noted above, and U.S. Pat. No. 5,646,327 (Burns et al). Many of these antioxidants are mono- and dialkylhydroxylamines having one or more substituents on one or both alkyl groups. Particularly useful alkyl substituents include sulfo, carboxy, amino, sulfonamido, carbonamido, hydroxy, and other solubilizing substituents.

More preferably, the noted hydroxylamine derivatives can be mono- or dialkylhydroxylamines having one or more hydroxy substituents on the one or more alkyl groups. Representative compounds of this type are described for example in U.S. Pat. No. 5,709,982 (Marrese et al), as having the structure I:

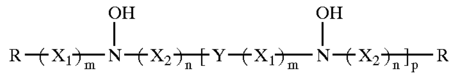

wherein R is hydrogen, a substituted or unsubstituted alkyl group of 1 to 10 carbon atoms, a substituted or unsubstituted hydroxyalkyl group of 1 to 10 carbon atoms, a substituted or unsubstituted cycloalkyl group of 5 to 10 carbon atoms, or a substituted or unsubstituted aryl group having 6 to 10 carbon atoms in the aromatic nucleus.

$X_1$ is —$CR_2(OH)CHR_1$— and $X_2$ is —$CHR_1CR_2(OH)$— wherein $R_1$ and $R_2$ are independently hydrogen, hydroxy, a substituted or unsubstituted alkyl group or 1 or 2 carbon atoms, a substituted or unsubstituted hydroxyalkyl group of 1 or 2 carbon atoms, or $R_1$ and $R_2$ together represent the carbon atoms necessary to complete a substituted or unsubstituted 5- to 8-membered saturated or unsaturated carbocyclic ring structure.

Y is a substituted or unsubstituted alkylene group having at least 4 carbon atoms, and has an even number of carbon atoms, or Y is a substituted or unsubstituted divalent aliphatic group having an even total number of carbon and oxygen atoms in the chain, provided that the aliphatic group has a least 4 atoms in the chain.

Also in Structure I, m, n and p are independently 0 or 1. Preferably, each of m and n is 1, and p is 0.

Specific di-substituted hydroxylamine antioxidants include, but are not limited to, N,N-bis(2,3-dihydroxypropyl)hydroxylamine, N,N-bis(2-methyl-2,3-dihydroxypropyl)hydroxylamine and N,N-bis(1-hydroxymethyl-2-hydroxy-3-phenylpropyl)hydroxylamine. The first compound is preferred.

It is also contemplated that the process of the invention may be advantageously used in preparing polymer latex containing layers in combination with the specific materials and processes described in an article titled "Typical and Preferred Color Paper, Color Negative, and Color Reversal Photographic Elements and Processing," published in Research Disclosure, February 1995, Volume 370.

Color paper elements typically contain less than 0.80 g/m<2> of total silver. Due to the need to decrease the environmental impact of color paper processing, it is desired to decrease the amount of total silver used in the element as much as possible. Therefore, total silver levels of less than 0.65 g/m<2> are preferable, and levels of 0.55 g/m<2> are even more preferable. It is possible to reduce further the total silver used in the color paper photographic element to less than 0.10 g/m<2> by use of a so-called development amplification process whereby the incorporated silver is used only to form the latent image, while another oxidant, such as hydrogen peroxide, serves as the primary oxidant to react with the color developer. Such processes are well known to the art, and are described in, for example, U.S. Pat. Nos. 4,791,048, 4,880,725, and 4,954,425, EP 487,616, International Published Patent Applications Nos. WO 90/013,059, 90/013,061, 91/016,666, 91/017,479, 92/001,972, 92/005, 471, 92/007,299, 93/001,524, 93/011,460, and German published patent application OLS 4,211,460.

In a preferred embodiment, the poultry gelatin is located in the upper half of the imaging member. More preferably, the poultry gelatin is located in at least one of the top three layers, typically the overcoat layer, the UV layer, or the cyan layer. Typically the uppermost layers are non-imaging layers, farthest from the support, which serve to provide protection to the unprocessed element as well as to the processed element. The poultry gelatin is most preferably located in the overcoat layer or top layer of the imaging element as this layer is unbounded at the air interface, and is most likely to result in reticulation patterns which degrade gloss and haze performance.

The amount of poultry gelatin in the layer is between 10–100% by weight of any one layer. More preferably, the gelatin is present in between 50–100% by weight of any one layer To provide the greatest enhancement in gloss benefits, as well as Theological benefits when coating the element. Most preferably, the gelatin is present in greater than 90% by weight of any one layer. The balance of the gelatin present in the layer containing poultry gelatin may include other gelatins, such as non-poultry gelatin, acid-processed bovine gelatin, lime-processed bovine and combinations thereof. Preferred is lime-processed bovine gelatin.

The layers containing the poultry gelatin of the present invention may contain other ingredients. These ingredients may be as described in the preceding paragraphs relating to the preparation of imaging layers containing light-sensitive silver grains and dye-forming couplers. In the preferred embodiment, the overcoat may contain additional ingredients such as silica, polymeric particles, lubricant dispersion particles such as polydimethylsiloxane particles, and surfactants. The colloidal silica may have a particle size of less than 1 micron, preferably less than 0.1 micron, more preferably less than 0.05 micron. The colloidal silica is present from 10% to 40% by weight of the total gelatin and colloidal silica (i.e. a weight ratio of gelatin to silica comprises 9:1 to 6:4), preferably from 15% to 35%, most preferably from 20% to 30%. The surfactant is preferably an anionic or nonionic surfactant, including fluorosurfactants. For purposes of this invention, a surfactant is a surface-active material, which is capable of depressing the surface tension of distilled water by at least 20 dynes/cm at its critical micelle concentration at 25° C. Anionic surface active agents preferably have the —$SO_3$<−> or —$OSO_3$<−> moiety. Preferred anionic surface active agents include naphthalenesulfonic acids, sulfosuccinic acids, alkylbenzenesulfonic acids, alylsulfonates, alkylsulfates and alkylbenzenesulfonates. Most preferred surfactants are naphthalenesulfonic acids and sulfosuccinic acids Preferred nonionic surface active agents include polyol compounds, and compounds of the formula R—O—(CH2CH2O)[n]H where R is alkyl, aryl or aralkyl and n is from 5 to 30. A useful embodiment of the invention incorporates block copolymers of polyoxypropylene and polyoxyethylene in one of the layers such as in the overcoat. Examples of such materials are described in U.S. Pat. No. 5,491,052 and include Pluronic L44 of BASF Inc. (SF-8 below). A suitable amount of the surface active agent is up to 50% based on the gelatin used, preferably up to 20% and most preferably up to 10%.

SF-1

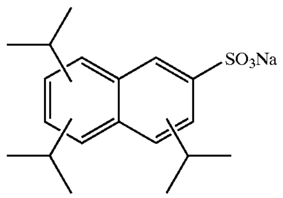

SF-2

$CF_3•(CF_2)_7•SO_3Na$

SF-3

$CH_3•(CH_2)_n•SO_3Na$, n = 12–14

SF-4

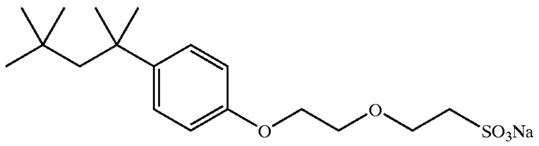

SF-5

$CH_3•(CH_2)_{11}•OSO_3Na$

SF-6

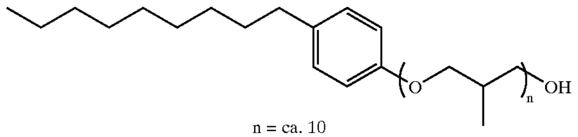

n = ca. 10

-continued

SF-7

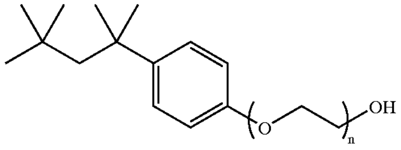

n = ca. 40

SF-8

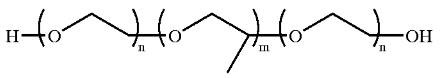

n = ca. 6, m = ca. 2

SF-9

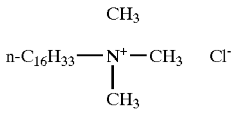

SF-10

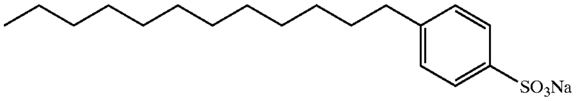

SF-11

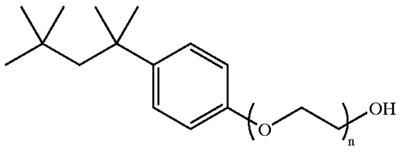

n = ca. 10

SF-12

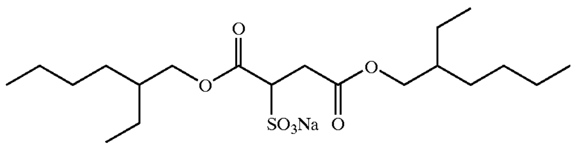

SF-13

Mixture of $F_3C—(CF_2)_5—CH_2—CH_2—SO_3H$ and $F_3C—(CF_2)_5—CH_2—CH_2—SO_3H$ $\cdot NH_3$ Various types of hardeners are useful in conjunction with elements of the invention. In particular, bis(vinylsulfonyl) methane, bis(vinylsulfonyl)methyl ether, 1,2-bis (vinylsulfonyl-acetamido)ethane, 2,4-dichloro-6-hydroxy-s-triazine, triacryloyltriazine, and pyridinium, 1-(4-morpholinycarbonyl)-4-(2-sulfoethyl)-, inner salt are particularly useful. Also useful are so-called fast acting hardeners as disclosed in U.S. Pat. Nos. 4,418,142, 4,618,573, 4,673,632, 4,863,841, 4,877,724, 5,009,990, 5,236,822.

An embodiment of the invention may provide an improvement in upper surface gloss value of greater than 1% and/or an improvement in haze value of greater than 5%, when compared to a similarly dried coated element of an acid-treated bovine gelatin with an isoelectric point of 6.5–7.5, where the only change in the image elements being compared is the gelatin in the upper layers.

The preferred embodiment of the present invention provides an aqueous coating composition comprising poultry gelatin, which provides enhanced melt stability, especially at higher concentrations of gelatin. The present invention enables increasing the concentrations of a coating fluid containing gelatin and dispersed sub-micron colloidal materials, reducing the size of the sub-micron colloidal materials in such a coating fluid, and/or including higher molecular weight gelatin in such a coating fluid without detrimentally increasing the viscosity of such fluids. The invention further enables reducing the viscosity of an aqueous coating fluid containing gelatin and dispersed insoluble colloidal material, without needing to reduce the concentration of gelatin or colloidal materials, increase the size of the sub-micron colloidal materials, and/or reduce the molecular weight of the gelatin. Each such advantage may be achieved either individually, or in combinations to varying extents, without the need to fundamentally change the composition of the materials in the coating fluid.

The aqueous coating compositions in accordance with the invention comprise from between 1% and 25% by weight poultry gelatin, preferably from 3% to 20%, most preferably from 5% to 20% weight. The aqueous coating compositions may additionally comprise acid-processed or lime-processed bovine gelatins, in amounts that are preferably less than 75% by weight of the total gelatin, more preferably less than 50%, and most preferably less than 25% by weight.

The aqueous coating compositions in accordance with the invention may additionally comprise colloidal silica having a particle size of less than 1 micron, preferably less than 0.1 micron, more preferably less than 0.05 micron. The colloidal silica is present from 10% to 40% by weight of the total gelatin and colloidal silica (i.e. a weight ratio of gelatin to silica comprises 9:1 to 6:4), preferably from 15% to 35%, most preferably from 20% to 30%.

The aqueous coating compositions in accordance with the invention may additionally comprise at least 0.01 volume fraction of a colloidal dispersed hydrophobic material phase. The dispersed hydrophobic material may be a dispersion of any colloidal organic or inorganic material useful in imaging elements, and in particular photographically useful materials, such as dispersed photographic coupler drops, UV-absorbers, scavengers of oxidized developer, silver halide grains, dye particles or other materials needed for other functions in an imaging element, such as polymer latexes and silica particles. The invention is particularly useful with respect to coating fluids comprising dispersed hydrophobic material wherein the number mean particle diameter of dispersed hydrophobic colloidal material comprising at least 0.01 volume fraction is less than 0.6 micrometer, and more particularly less than 0.3 micrometer, and more preferably where dispersed colloidal material of such mean particle sizes comprise a volume fraction of the coating fluid of at least 0.03, as such coating fluids are generally more liable to otherwise result in higher than desired coating viscosities as a result of interactions between the gelatin and the dispersed hydrophobic material phase. Preparation of the colloidal dispersions of hydrophic materials for use in the coating fluids of the invention is itself not critical, and any known dispersion forming techniques (e.g., high pressure emulsification, mill grinding, precipitation.) may be used. Lubricant particle of greater than 3 microns may also be contained in the aqueous coating composition, prepared by conventional techniques, or in a preferred embodiment, prepared using a limited coalescence technique as described in U.S. Pat. No. 5,541,048. Whether a small particle size or a large particle size lubricant is used, the preferred lubricant is polydimethylsiloxane.

The coating melt may include surfactants. The surfactants are preferably an anionic or nonionic surfactant, including fluorosurfactants. For purposes of this invention, a surfactant is a surface-active material, which is capable of depressing the surface tension of distilled water by at least 20 dynes/cm at its critical micelle concentration at 25° C. Anionic surface active agents preferably have the —$SO_3$<–> or —$OSO_3$<–> moiety. Preferred anionic surface-active agents include naphthalenesulfonic acids, sulfosuccinic acids, alkylbenzenesulfonic acids, alylsulfonates, alkylsulfates and alkylbenzenesulfonates. Most preferable anionic surfactants are naphthalenesulfonic acids and sulfosuccinic acids. Preferred nonionic surface-active agents include polyol compounds, and compounds of the formula R—O—(CH2CH2O)[n]H where R is alkyl, aryl or aralkyl and n is from 5 to 30. A useful embodiment of the invention incorporates block copolymers of polyoxypropylene and polyoxyethylene in one of the layers such as in the overcoat. Examples of such materials are described in U.S. Pat. No. 5,491,052 and include Pluronic L44 of BASF Inc. (SF-8 below). A suitable amount of the surface active agent is up to 50% based on the gelatin used, preferably up to 20% and most preferably up to 10.

SF-1

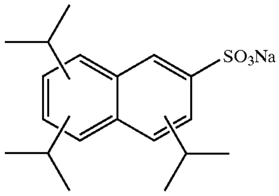

SF-2

$CF_3 \bullet (CF_2)_7 \bullet SO_3Na$

SF-3

$CH_3 \bullet (CH_2)_n \bullet SO_3Na$, n = 12–14

SF-4

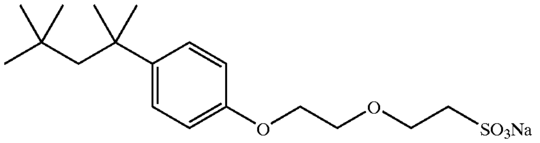

SF-5

$CH_3 \bullet (CH_2)_{11} \bullet OSO_3Na$

SF-6

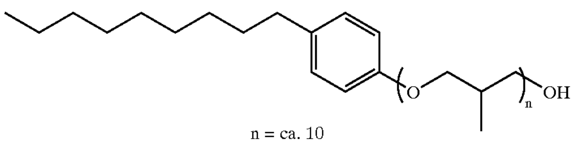

n = ca. 10

SF-7

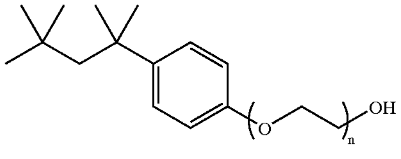

n = ca. 40

SF-8

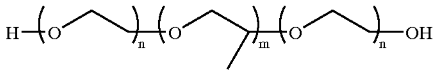

n = ca. 6, m = ca. 2

-continued

SF-9

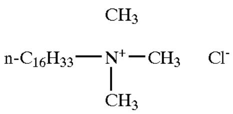

SF-10

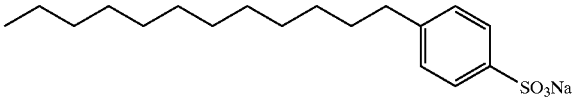

SF-11

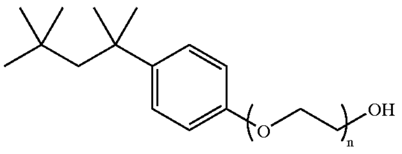

n = ca. 10

SF-12

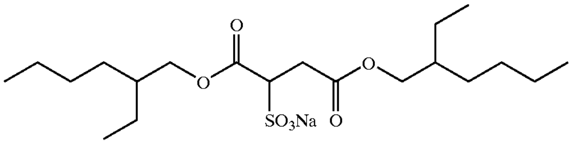

SF-13

Mixture of $F_3C—(CF_2)_5—CH_2—CH_2—SO_3H$ and $F_3C—(CF_2)_5—CH_2—CH_2—SO_3H$ $\bullet NH_3$ Devices suitable for the high-shear or turbulent mixing of the dispersions of the invention include those generally suitable for preparing submicron photographic emulsified dispersions. These include but are not limited to blade mixers, colloid mills, homogenizer devices in which a liquid stream is pumped at high pressure through an orifice or interaction chamber, sonication, Gaulin mills, homogenizers, blenders, microfluidizers, rotor stator devices. More than one type of device may be used to prepare the dispersions. For the purposes of this invention, "high shear or turbulent conditions" defines shear and turbulence conditions sufficient to generate a small particle conventional photographic dispersion with an average particle size of less than about 0.5 micron.

In addition to gelatin, other water-soluble polymers or copolymers may be included in the coating compositions of the invention, such as poly(vinyl alcohol), partially hydrolyzed poly(vinylacetate/vinylalcohol), hydroxyethyl cellulose, poly(acrylic acid), poly(1-vinylpyrrolidone), poly (sodium styrene sulfonate), poly(2-acrylamido-2-methane sulfonic acid), polyacrylamide. Copolymers of these polymers with hydrophobic monomers may also be used.

The following examples are provided to illustrate the invention.

EXAMPLE 1

Stock solutions were made up as follows:

Water was added to dry gelatin granules, which were allowed to soak in a refrigerator for a minimum of 30 minutes and a maximum of 3 days. Samples were then placed in a controlled temperature bath at 50° C. and allowed to melt. The sample hold time in the CTB was between 30 and 120 minutes, with longer times necessary for uniform melting, mixing and removal of bubbles from higher viscosity solutions. Samples not used immediately were stored at 5° C. for up to a maximum of four days.

The rheological measurements were made with a controlled stress Bohlin CS-50® rheometer. A bob-and-cup measuring geometry (C2.3/26) was used throughout. Temperature was regulated to an accuracy of 0.1° C. Viscosity is measured by applying a given torque to the bob and measuring the resulting rotation rate. From the dimensions of the geometry, torque may be translated into shear stress, and rotation speed into shear rate. Where silica was a component of the fluids, it was always added last.

To monitor the consistency of the performance of the rheometers, the viscosity of a standard oil was measured each day prior to making measurements on the melts. The oil was supplied by Poulton Selfe and Lee and had a viscosity of 82.92–0.4 mPa.s (cPs) at 40.0° C., measured by capillary viscometry against traceable standards. The standard deviation of the oil viscosity on the CS50 was better than 1%. Most of the measurements in this report were made with the CS50.

The sample was removed from the 50° C. constant-temperature bath and 3 mL placed into the cup using a warmed glass syringe. The pre-warmed bob was lowered into the sample, any surface bubbles removed, and six drops of hexadecane placed on the liquid surface. Hexadecane prevents surface skin formation and dehydration, while having a negligible effect on viscosity. Finally, a heat shield was placed on top of the cup to minimize further evaporation and heat loss.

The sample was initially held at 50° C. and allowed to equilibrate. Thermal equilibrium was assumed to be achieved when viscosity did not change as a function of time, which was usually within 5 minutes of loading the sample into the cup. A small shear stress or rate (typically 0.82 Pa) was applied continuously to the sample, and the viscosity measured at 15-second intervals for 15 minutes at 50° C., a high and steady temperature. The temperature was then lowered by 1° C. Once the CTB was within 0.5° C. of the new lower temperature (within a minute), the viscosity was again recorded for a further 15 minutes. This process was repeated until the temperature had fallen to 35° C. or a viscosity rise of at least 2% over the 15-minute period was measured.

The data were interpreted as follows:

First, the measurements for the first three minutes at any given temperature were discounted, as thermal equilibration within the sample was not complete. Then, the time dependence of the viscosity data between 3 and 15 minutes was determined by linear regression. At elevated temperatures, the viscosity is independent of time (within +/−1% of zero) and increases as temperature falls according to Arrhenius-type behavior (an exponential rise in viscosity as reciprocal absolute temperature increases). As the temperature was lowered further, the increase in viscosity is faster than expected from the Arrhenius expression and the viscosity increased with time over the period 3 to 15 minutes after attaining temperature. The rate of rise of viscosity (expressed as percentage change over 15 minutes) was determined for each temperature. From a plot of rate of viscosity rise against temperature, the temperature at which the viscosity increases by 2% over 15 minutes was determined. This is defined as the viscosity-rise temperature, referred to as T2%. This temperature is several degrees above that at which elasticity develops within the sample over a 15-minute period. The viscosity rise is associated with the aggregation of gelatin molecules, and on longer holds, particularly in the presence of colloidal addenda, can give rise to the formation of aggregates of dimensions of microns that cause coating defects. Therefore, it is important that the coating solutions are held at temperatures above T2% prior to coating. The T2% value of a coating solution can be reduced by reduction in viscosity V45, for example by dilution. Dilution is disadvantageous because of the increase loading on the dryer, which increases energy costs and may limit the maximum manufacturing speed. The other important characteristic for the sample is the viscosity at 45° C., V45. This single value incorporates the effect of both gelatin concentration and gelatin molecular weight.

All gelatins had been de-calcified and were supplied at a pH of 5.7. Gelatin samples were provided by a range of manufacturers. Concentrations quoted are of the granules that had been stored at ambient conditions and therefore contained approximately 10% water. The gelatins had similar viscosity-average molecular weights, in particular gelatins A, B, C, and G for which most detailed comparative studies were made. The gel strength of the gelatins was at least 270 g.

The table below specifies gelatins A–K. The gelatins of this table will be referred to in all the examples, which follow.

| Gelatin | Bone | Treatment | pI | Viscosity (6.16% gelatin) | Supplier |
|---|---|---|---|---|---|
| A | Cattle | Lime-processed | 4.9–5.2 | 5.5. mPa · s (cPs) | S1 |
| B | Cattle | acid-processed | 7.67 | | S1 |
| C | Cattle | acid-processed | 7.45 | | S2 |
| D | Cattle | acid-processed | 8.4 | | S1 |
| E | Cattle | acid-processed | 8.1 | | S2 |
| F | Cattle | acid-processed | 8.5 | | S3 |
| G | Cattle | acid-processed | 8.0–8.5 | | S4 |
| H | Poultry | acid-processed | 8.5 | | S1 |
| K | Poultry | acid-processed | 8.1 | | S1 |

TABLE 1

Concentration, solution viscosity at 45° C. and viscosity-rise temperature of solutions of different gelatins at a range of concentrations.

| Concentration % w/w | Viscosity at 45° C., V45 mPa · s (cPs) | Viscosity-rise temperature, T2% ° C. |
|---|---|---|
| | Gelatin A | |
| 5 | 3.1 | 31.6 |
| 8 | 6.3 | 33.7 |
| 10 | 9.8 | 34.2 |
| 15 | 26.4 | 36.8 |
| 20 | 68.4 | 38.4 |
| 20 | 63.2 | 38.2 |
| 20 | 70.0 | 38.5 |
| 25 | 153.7 | 39.2 |
| 30 | 348.3 | 40.4 |
| | Gelatin B | |
| 15 | 28.5 | 37.8 |
| 20 | 72.7 | 39.5 |
| 25 | 181 | 41.0 |
| | Gelatin C | |
| 10 | 11.1 | 39.8 |
| 10 | 10.6 | 39.6 |
| 15 | 30.4 | 41.6 |
| 18 | 46.9 | 41.8 |

TABLE 1-continued

Concentration, solution viscosity at 45° C. and viscosity-rise temperature of solutions of different gelatins at a range of concentrations.

| Concentration % w/w | Viscosity at 45° C., V45 mPa · s (cPs) | Viscosity-rise temperature, T2% ° C. |
|---|---|---|
| 20 | 74.3 | 41.8 |
| 20 | 73.0 | 42.5 |
| 20 | 71.0 | 41.5 |
| 20 | 73.0 | 42.0 |
| 23 | 103.6 | 42.7 |
| 25 | 206.4 | 42.8 |
| 30 | 373.8 | 44.3 |
| | Gelatin D | |
| 10 | 12 | 40.9 |
| 15 | 39.7 | 42.4 |
| 20 | 115.8 | 42.9 |
| | Gelatin E | |
| 10 | 8.8 | 39.2 |
| 15 | 24.8 | 40.9 |
| 20 | 67.1 | 42.0 |
| | Gelatin F | |
| 10 | 10.8 | 40.2 |
| 20 | 92.1 | 43.1 |
| | Gelatin G | |
| 10 | 11.1 | 38.5 |
| 15 | 30.0 | 41.0 |
| 18 | 52.9 | 41.8 |
| 20 | 85.9 | 41.9 |
| 25 | 202.0 | 42.8 |
| | Gelatin H | |
| 10 | 10.7 | 35.8 |
| 15 | 31.5 | 37.8 |
| 20 | 76 | 39.0 |
| 20 | 71 | 39.0 |
| 25 | 213 | 39.9 |
| 30 | 496 | 41.0 |

The value of the viscosity rise temperature increases with solution viscosity. The values of T2% of solutions of Gelatin A, the lime-processed bovine osseine gelatin, are lower than for the acid-processed gelatins (B to H) with similar values of V45. The values of T2% of solutions of gelatin B (an acid-vine processed bovine osseine gelatin) and gelatin H (an acid-processed poultry osseine gelating) lower than those of the acid-processed bovine osseine gelatins C to G. Therefore, gelatins B and H are advantaged over the other gelatins on the basis of enabling a lower holding temperature for coating solution of given V45.

The underlying layers in a photographic coating pack usually contain lime-processed bovine osseine gelatin. The optimal coating quality occurs when the top-layer coating fluid viscosity matches that of the fluids comprising the underlying layers and when the fluids are coated at the same temperature. However, if gelatins C to G are used in formulating the top layer coating fluid at a given V45, the T2% values are between 3 and 4° C. higher than that of the underlying layers, thereby necessitating reduction in viscosity of the top layer by dilution or coating of that solution at a higher temperature.

EXAMPLE 2

Coating fluids containing gelatin and Ludox AM® (supplied by DuPont) were formulated at a constant ratio of gelatin:silica (7:3 by weight). The temperature-dependent behavior of the viscosity was measured by the same method as in Example 1.

TABLE 2

Concentration, solution viscosity at 45° C. and viscosity-rise temperature of solutions of different gelatins at a range of concentrations at a constant ratio of 7:3 by weight gelatin:silica.

| Gelatin Concentration % w/w | Viscosity at 45° C., V45 mPa · s (cPs) | Viscosity-rise temperature, T2% ° C. |
|---|---|---|
| | Gelatin A | |
| 10 | 25.9 | 37.4 |
| 15 | 131.9 | 38.9 |
| | Gelatin B | |
| 10 | 28.6 | 40.0 |
| 13 | 80.1 | 40.8 |
| 15 | 154.4 | 42.2 |
| | Gelatin C | |
| 10 | 33.2 | 42.8 |
| 15.6 | 134.0 | 43.8 |
| | Gelatin H | |
| 10 | 24.0 | 38.4 |
| 15 | 101.0 | 39.6 |
| 18 | 209.0 | 39.8 |

For these coating fluids, it can be seen that the value of T2% at comparable viscosity increases in the order of gelatins A<H<B<C. Thus, of the acid-processed gelatins, the poultry gelatin sample has the lowest value of the viscosity-rise temperature.

EXAMPLE 3

Full formulations suitable for coating as the top layer of a photographic paper were prepared at gelatin:silica ratios of 7:3 and 8:2 at gelatin concentrations of 14.0 and 16.2%, respectively. The details of the compositions are given in Table 3. The lubricant polydimethylsiloxane was supplied in dispersion of 0.1 micron particles formed with standard homogenization techniques. The disperson contained 13.35% polydimethylsiloxane, 1.34% Tergitol 15-S-5™ (ethoxylated secondary alcohol), 8.16% lime-processed osseine gelatin, and 19.08% Alkanol XC™.

TABLE 3

Composition of coating used (by mass in grams).

| | Fluid | | | |
|---|---|---|---|---|
| | I | J | K | L |
| | Gelatin | | | |
| | C* | C* | H | H |
| Gelatin % | 14.02% | 16.24% | 14.02% | 16.24% |
| Silica % (Ludox AM) | 6.00% | 4.03% | 6.00% | 4.03% |
| Dispersion of polydimethylsiloxane | 3.85% | 3.89% | 13.19 | 13.35 |
| Kathon LS ™ | 10 ppm | 10 ppm | 10 ppm | 10 ppm |
| SF-1 | 0.2% | 0.2% | 0.2% | 0.2% |
| SF-2 | 0.08% | 0.06% | 0.08% | 0.06% |
| SF-12 | 0.1% | 0.00 | 0.1% | 0.00 |
| | Comparison | Comparison | Invention | Invention |

In the same rheological equipment as above, these coating fluids were cooled from 45° C. to 40° C. at 1° $C.min^{-1}$. The viscosity was then recorded with time at 40° C. at a constant stress of 1 Pa. The sample completed thermal equilibration during the first 300 s after reaching 40° C. A linear regression was applied to the values of viscosity measured between 300 s and 2000 s after cooling to 40° C., and the fit parameters are given in Table 4.

TABLE 4

Time-dependence of viscosity of coating fluids after cooling to 40° C.

| Coating Fluid | Gelatin | V45 mPa · s (cPs) | V(at 0 s) at 40° C. mPa · s (cPs) | Viscosity change at 40° C. %/15 min |
|---|---|---|---|---|
| I | C | 156 | 258 | +16.9 |
| K | H | 158 | 229 | +3.0 |
| J | C | 128 | 202 | +16.3 |
| L | H | 123 | 171 | +2.9 |

Fluids I and J, which contained gelatin C, showed a greater dependence of viscosity on temperature under these conditions. Therefore, gelatin H is advantaged in terms of hold temperature at a given viscosity.

EXAMPLE 4

The onset of the temperature-dependent viscosity rise of coating fluids I to L at different concentrations was characterized more fully by determination of the viscosity-rise temperature as described above. These experiments were carried out with the fluids at a range of concentrations, following dilution with water. The results are given in Table 5.

TABLE 5

Viscosity and viscosity-rise temperature of coating fluids at different concentrations.

| Gelatin Concentration % w/w | Viscosity at 45° C., V45 mPa · s (cPs) | Viscosity-rise temperature, T2% ° C. |
|---|---|---|
| | Fluid K and dilutions | |
| 14.0 | 163.0 | 40.5 |
| 13.1 | 132.0 | 40.6 |
| 12.3 | 91.0 | 40.1 |
| 10.9 | 56.8 | 39.8 |
| 9.8 | 38.3 | 39.7 |
| | Fluid I and dilutions | |
| 14.0 | 157.0 | 44.4 |
| 9.8 | 34.0 | 43.9 |
| | Fluid L and dilutions | |
| 16.2 | 129.0 | 40.6 |
| 11.4 | 37.4 | 39.5 |
| | Fluid J and dilutions | |
| 16.2 | 129.0 | 44.2 |
| 11.4 | 31.6 | 43.5 |

Fluids K and L, which contain the acid-processed poultry gelatin (H), show a lower viscosity-rise temperature even at much higher concentrations and viscosities than the corresponding fluids I and J that were made with the acid-processed bovine osseine gelatin (C). Therefore, gelatin H is advantaged in permitting the formation of fluids of higher viscosity and lower viscosity-rise temperature.

EXAMPLE 5

A color-negative imaging element on a reflective support 516 was prepared using primarily conventionally prepared lime-processed gelatins in the hydrophilic colloid layers thereof, except for the overcoat. The support was photographic grade paper resin coated with polyethylene on the front and back sides. The face-side resin layer on the support contained titanium dioxide, red and blue colorants, a fluorescent optical brightener, and antioxidants. In the coating structure, a blue imaging layer consisting of yellow coupler mixed with a blue-sensitive chloro-iodide cubic emulsion (0.2 mol % iodide, 0.6 μm average grain size) was the first layer of a three-color photographic recording material on the resin-coated paper support. The subsequent layers consisted, in order, of a layer containing a scavenger for oxidized developer, a green imaging layer, a second scavenger layer, a red imaging layer, a UV absorbing layer and a protective gelatin super-coat. The green imaging layer consisted of a dispersion of magenta coupler mixed with a green-sensitive chloride cubic emulsion (0.3 μm average grain size) while a red-sensitized chloride emulsion (0.4 μm average grain size) was mixed with a dispersion of cyan couplers to form the red imaging layer. Details of the structure of the multilayer coating, including component coverages in each layer, are shown below. The gelatin used in the overcoat was acid-processed osseine gelatin C, Example 1. The gelatin was delivered from a melt similar to coating fluid J in Example 3 above.

Elements 501–515, 517–524 were prepared as element 516, except replacing the gelatin and adding silica as specified in the table below. Elements 513–524 contained colloidal silica and were coated at the same gelatin laydown as their corresponding elements 501–512 which did not contain colloidal silica.

| Coating structure | |
|---|---|
| Layer 7 (Supercoat) | |
| Ludox AM ® colloidal silica (DuPont) (elements 513–512 only) | 0.1614 g · m$^{-2}$ |
| Gelatin (acid-processed gelatin C) | 0.6456 g · m$^{-2}$ |
| Polydimethylsiloxane (from dispersion as in example 4) | |
| SF-1 | 0.0080 g · m$^{-2}$ |
| SF-2 | 0.0033 g · m$^{-2}$ |
| Layer 6 (UV Layer) | |
| Tinuvin-328 ® | 0.130 g · m$^{-2}$ |
| Tinuvin 326 ® | 0.023 g · m$^{-2}$ |
| DMBHQ | 0.042 g · m$^{-2}$ |
| CS-3 | 0.051 g · m$^{-2}$ |
| Gelatin | 0.525 g · m$^{-2}$ |
| Layer 5 (Red-sensitive Layer) | |
| Ag | 0.198 g · m$^{-2}$ |
| Coupler CC-1 | 0.232 g · m$^{-2}$ |
| Coupler CC-2 | 0.026 g · m$^{-2}$ |
| Tinuvin 328 ® | 0.355 g · m$^{-2}$ |
| CS-3 | 0.145 g · m$^{-2}$ |
| CS-4 | 0.436 g · m$^{-2}$ |
| Gelatin | 1.312 g · m$^{-2}$ |
| Layer 4 (Interlayer B) | |
| DMBHQ | 0.108 g · m$^{-2}$ |
| CS-2 | 0.197 g · m$^{-2}$ |
| Gelatin | 0.753 g · m$^{-2}$ |
| Layer 3 (Green-sensitive Layer) | |
| Ag | 0.099 g · m$^{-2}$ |
| Coupler MC-1 | 0.208 g · m$^{-2}$ |
| St-4 | 0.040 g · m$^{-2}$ |
| St-3 | 0.274 g · m$^{-2}$ |
| CS-5 | 0.218 g · m$^{-2}$ |
| CS-2 | 0.112 g · m$^{-2}$ |
| Gelatin | 1.187 g · m$^{-2}$ |

-continued

| Coating structure | |
|---|---|
| Layer 2 (Interlayer A) | |
| DMBHQ | 0.108 g · $m^{-2}$ |
| CS-2 | 0.197 g · $m^{-2}$ |
| Gelatin | 0.753 g · $m^{-2}$ |
| Layer 1 (Blue-sensitive Layer) | |
| Ag | 0.217 g · $m^{-2}$ |
| Coupler YC-1 | 0.414 g · $m^{-2}$ |
| St-5 | 0.121 g · $m^{-2}$ |
| Latex copolymer | 0.414 g · $m^{-2}$ |
| CS-1 | 0.218 g · $m^{-2}$ |
| HQ-K | 0.0095 g · $m^{-2}$ |
| PHR | 0.0011 g · $m^{-2}$ |
| Gelatin | 1.244 g · $m^{-2}$ |
| Hardener | 0.125 g · $m^{-2}$ |

-continued

| Coating structure |
|---|
| Resin layer: polyethylene and titanium dioxide, red and blue colorants, fluorescent optical brightener, antioxidants |
| Paper Support<br>Resin layer: polyethylene |
| antistatic layer |

Latex copolymer = 50/50 t-butylacrylamide/t-butylacrylate latex copolymer

PHR = 2,5-dihydroxy-5-methyl-3-(1-piperidenyl)-2-cyclopenten-1-one

HQ-K = 2,5-dihydroxy-4-(1-methylheptadecyl)-benzenesulphonic acid (K salt)

DMBHQ = 2,5-di-(1,1,3,3-tetramethylbutyl) hydroquinone

Hardener = bis(vinylsulphonyl) methane (BVSM)

Stabilizer St-1

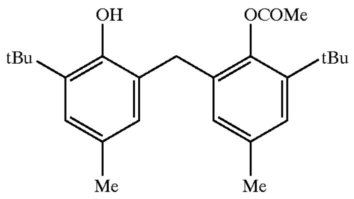

Stabilizer St-2

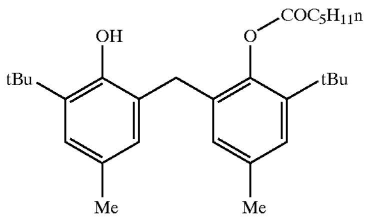

Stabilizer St-3

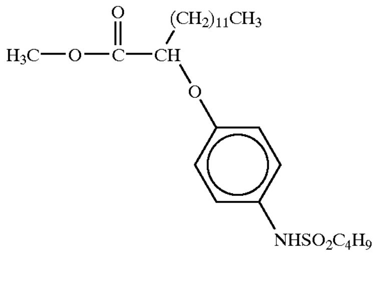

Stabilizer St-4

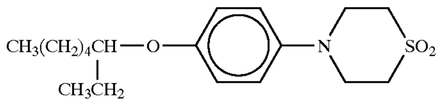

-continued
Stabilizer St-5
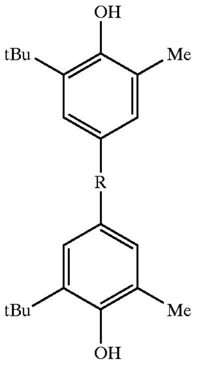
R =
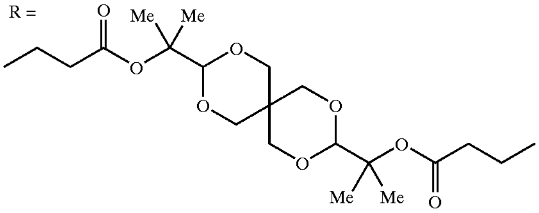
St-6 Irganox 1076 ®
Solvent CS-1
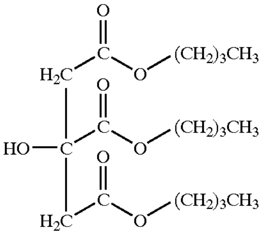
Solvent CS-2
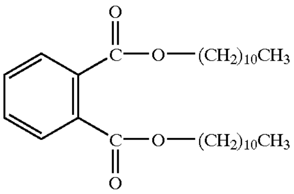
Solvent CS-3
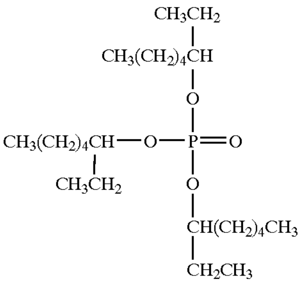
Solvent CS-4
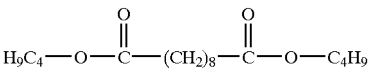
Solvent CS-5 $CH_3(CH_2)_7CH{=}CH(CH_2)_8{-}OH$
CS-6 Tritolyl phosphate -continued Coupler YC-1

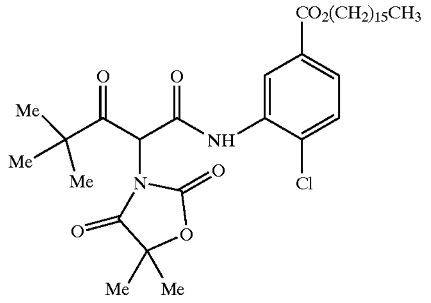

Coupler MC-1

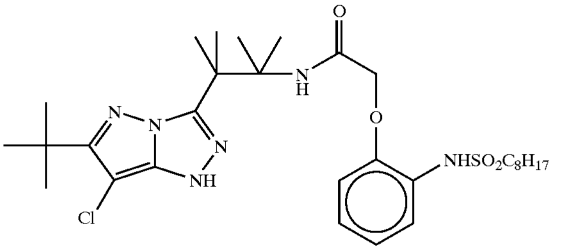

Coupler CC-1

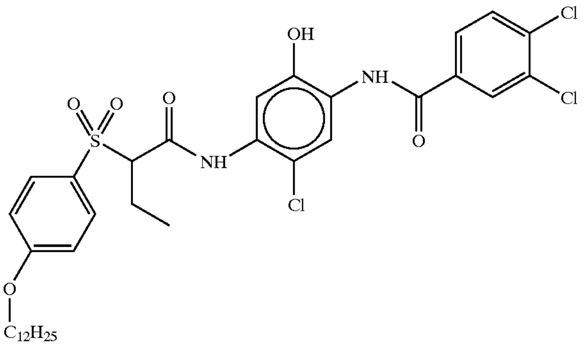

Coupler CC-2

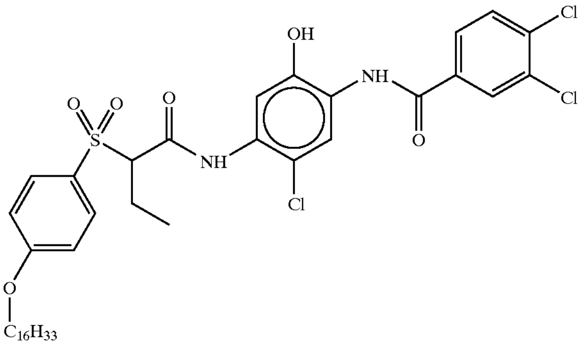

Samples were prepared using the same underlying layers, varying only the overcoat composition as specified in the table below. The drying conditions in the drying section of the coating machine were adjusted to control the average web temperature from the point at which the coating is an average of 15% gelatin to the point where it is 65% gelatin. This is reported as the drying temperature in the table below, where a higher temperature is harsher.

Samples of coating elements were processed in RA-4 chemistry after exposing the samples to white light to form a neutral image at maximum density (about 2.2). The samples were dried with a conventional dryer process at 91° C. The gloss of the top surface was measured using a Gardner Micro Trigloss meter at an angle of illumination/reflection of 20°. The results are related to a highly polished black glass with a refractive index of 1.567 that has a specular gloss value of 100. Haze values were measured simultaneously with the gloss measurements, by measuring gloss at angle of illumination/reflection of 60°. The difference between the gloss at 60 and at 20° is reported as the haze.

Reticulation of the samples was evaluated by visually examining a surface photomicrograph taken under 100× magnification using bright-field optical microscopy. Values of 1–5 were assigned, where I shows little to no reticulation, 3 is moderately reticulated, and 5 is severely reticulated.

Measurements of gloss, haze, and reticulation were made 3 days, 7 days, and 14 days after coating. Visual inspection of the samples showed that gloss and haze are better correlated with image quality assessment, so a reticulation value of 5 may not necessarily be unacceptable. Therefore, comparison of gloss and haze data to the results of coatings with gelatin C under mild drying conditions would be most appropriate to assess the impact of the changes.

| | | SOC | % Silica in | Drying | Gloss | | | Haze | | | Reticulation | | |
|---|---|---|---|---|---|---|---|---|---|---|---|---|---|
| Element | | Gel | Overcoat | Temperature | 3D | 7D | 14D | 3D | 7D | 14D | 3D | 7D | 14D |
| 501 | Comp | A | 0 | 69 | 45.5 | 59.3 | 58.0 | 37.7 | 29.8 | 30.6 | 5 | 5 | 5 |
| 504 | Comp | C | 0 | 69 | 64.1 | 68.3 | 70.6 | 26.5 | 24.1 | 23.5 | 3 | 3 | 3 |
| 507 | Comp | E | 0 | 69 | 62.4 | 68.1 | 70.3 | 28.2 | 25.1 | 24.2 | 3 | 3 | 2 |
| 510 | Inv | H | 0 | 69 | 63.5 | 69.6 | 72.5 | 28.3 | 24.2 | 22.6 | 3 | 2 | 2 |
| 513 | Comp | A | 20 | 69 | 57.5 | 63.8 | 63.9 | 26.8 | 23.2 | 24.1 | 4 | 4 | 4 |
| 516 | Comp | C | 20 | 69 | 65.8 | 70.0 | 69.1 | 24.1 | 21.0 | 22.9 | 3 | 2 | 2 |
| 519 | Comp | E | 20 | 69 | 65.9 | 68.6 | 70.1 | 24.6 | 23.0 | 23.4 | 2 | 2 | 2 |
| 522 | Inv | H | 21.7 | 69 | 64.2 | 69.8 | 72.6 | 26.7 | 22.8 | 21.5 | 2 | 2 | 2 |
| 502 | Comp | A | 0 | 71 | 18.9 | 32.2 | 41.2 | 46.4 | 43.9 | 40.5 | 5 | 5 | 5 |
| 505 | Comp | C | 0 | 71 | 19.7 | 48.4 | 46.7 | 39.3 | 36.7 | 37.3 | 5 | 5 | 5 |
| 508 | Comp | E | 0 | 71 | 27.8 | 47.4 | 50.6 | 39.8 | 36.7 | 36.2 | 5 | 5 | 5 |
| 511 | Inv | H | 0 | 71 | 60.2 | 67.7 | 69.4 | 28.8 | 24.6 | 24.7 | 4 | 3 | 3 |
| 514 | Comp | A | 20 | 71 | 28.6 | 49.2 | 51.8 | 46.4 | 35.7 | 34.8 | 5 | 5 | 5 |
| 517 | Comp | C | 20 | 71 | 51.9 | 68.6 | 70.6 | 33.4 | 22.2 | 21.6 | 5 | 4 | 4 |
| 520 | Comp | E | 20 | 71 | 59.6 | 67.2 | 68.1 | 28.9 | 24.2 | 24.9 | 4 | 3 | 3 |
| 523 | Inv | H | 21.7 | 71 | 64.8 | 69.2 | 69.5 | 25.4 | 22.4 | 23.1 | 3 | 3 | 3 |

Comparing elements 501–503 with 504–506, acid-processed bovine gelatin C with an isoelectric point of 6.7 provides improved gloss, haze, and reticulation at a drying temperature of 69° F. (21° C.) over lime-processed bovine gelatin A. Elements 507–509 containing acid-processed bovine gelatin E with a higher isoelectric of 8.1 provide no additional improvement over gelatin C. Elements 510–512 comprising the acid-processed poultry gelatin H of the invention provide further and unexpected improvement in gloss, haze, and reticulation over both gelatins C and E, especially at the more harsh drying conditions resulting in a web temperature of 71° F. (22° C.).

The addition of colloidal silica to the coating melt solutions provided improvement in gloss, haze, and reticulation for gelatin A at the mildest drying conditions, but not at the more harsh conditions represented by the temperature of 71° F. (22° C.). Gelatins C and E of the prior art show improvements under the more harsh drying conditions. Gelatin H of the invention shows unexpected improvement in gloss, haze, and reticulation over both gelatins C and E, especially at 3 days after coating.

EXAMPLE 6

Color-negative imaging element on reflective support was prepared using primarily conventionally prepared lime-processed gelatins in the hydrophilic colloid layers thereof, except for the overcoat. The support was photographic grade paper resin coated with polyethylene on the front and back sides. The face-side resin layer on the support contained titanium dioxide, red and blue colorants, a fluorescent optical brightener, and antioxidants. In the coating structure, a blue imaging layer consisting of yellow coupler mixed with a blue-sensitive chloro-iodide cubic emulsion (0.2 mol % iodide, 0.6 μm average grain size) was the first layer of a three-color photographic recording material on the resin-coated paper support. The subsequent layers consisted, in order, of a layer containing a scavenger for oxidized developer, a green imaging layer, a second scavenger layer, a red imaging layer, a UV absorbing layer and a protective gelatin super-coat. The green imaging layer consisted of a dispersion of magenta coupler mixed with a green-sensitive chloride cubic emulsion (0.3 μm average grain size) while a red-sensitized chloride emulsion (0.4 μM average grain size) was mixed with a dispersion of cyan couplers to form the red imaging layer. Details of the structure of the multilayer coating, including component coverages in each layer, are shown below. The gelatin used in the overcoat was acid-processed osseine gelatin C. Where the amount of colloidal silica was 20% of the total weight of gelatin and colloidal silica, the layer was delivered from a melt similar to coating fluid J in example 3 above. When the amount of silica was 30% of the total gelatin and silica, the coating fluid was similar to fluid L. The gelatins used and laydowns of gelatin, silica, and surfactants are supplied in the table below.

| Coating structure | |
|---|---|
| Layer 7 (Supercoat) | |
| Ludox AM ® (DuPont) | $0.1614\ g \cdot m^{-2}$ |
| Gelatin (acid-processed gelatin C) | $0.6456\ g \cdot m^{-2}$ |
| SF-1 | $0.0080\ g \cdot m^{-2}$ |
| SF-2 | $0.0033\ g \cdot m^{-2}$ |
| Layer 6 (UV Layer) | |
| Tinuvin-328 ® | $0.130\ g \cdot m^{-2}$ |
| Tinuvin 326 ® | $0.023\ g \cdot m^{-2}$ |
| DMBHQ | $0.042\ g \cdot m^{-2}$ |
| CS-3 | $0.051\ g \cdot m^{-2}$ |
| Gelatin | $0.525\ g \cdot m^{-2}$ |
| Layer 5 (Red-sensitive Layer) | |
| Ag | $0.198\ g \cdot m^{-2}$ |
| Coupler CC-1 | $0.232\ g \cdot m^{-2}$ |
| Coupler CC-2 | $0.026\ g \cdot m^{-2}$ |
| Tinuvin 328 ® | $0.355\ g \cdot m^{-2}$ |
| CS-3 | $0.145\ g \cdot m^{-2}$ |
| CS-4 | $0.436\ g \cdot m^{-2}$ |
| Gelatin | $1.312\ g \cdot m^{-2}$ |
| Layer 4 (Interlayer B) | |
| DMBHQ | $0.108\ g \cdot m^{-2}$ |
| CS-6 | $0.197\ g \cdot m^{-2}$ |
| St-6 | |
| Gelatin | $0.753\ g \cdot m^{-2}$ |

-continued

| Coating structure | |
|---|---|
| Layer 3 (Green-sensitive Layer) | |
| Ag | 0.099 g · $m^{-2}$ |
| Coupler MC-1 | 0.208 g · $m^{-2}$ |
| St-4 | 0.040 g · $m^{-2}$ |
| St-3 | 0.274 g · $m^{-2}$ |
| CS-5 | 0.218 g · $m^{-2}$ |
| CS-2 | 0.112 g · $m^{-2}$ |
| Gelatin | 1.187 g · $m^{-2}$ |
| Layer 2 (Interlayer A) | |
| DMBHQ | 0.108 g · $m^{-2}$ |
| CS-6 | 0.197 g · $m^{-2}$ |
| St-6 | |
| Gelatin | 0.753 g · $m^{-2}$ |
| Layer 1 (Blue-sensitive Layer) | |
| Ag | 0.217 g · $m^{-2}$ |
| Coupler YC-1 | 0.414 g · $m^{-2}$ |
| St-1 | 0.080 g · $m^{-2}$ |
| St-4 | 0.080 g · $m^{-2}$ |
| St-5 | 0.080 g · $m^{-2}$ |
| CS-1 | 0.218 g · $m^{-2}$ |
| HQ-K | 0.0095 g · $m^{-2}$ |
| MHR | 0.0011 g · $m^{-2}$ |
| Gelatin | 1.244 g · $m^{-2}$ |
| Hardener | 0.125 g · $m^{-2}$ |

-continued

| Coating structure |
|---|
| Resin layer: polyethylene and titanium dioxide, red and blue colorants, fluorescent optical brightener, antioxidants |
| Paper Support |
| Resin layer: polyethylene |
| antistatic layer |

MHR = 2,5-dihydroxy-5-methyl-3-(4-morpholinyl)-2-cyclopenten-1-one
HQ-K = 2,5-dihydroxy-4-(1-methylheptadecyl)-benzenesulphonic acid (K salt)
DMBHQ = 2,5-di-(1,1,3,3-tetramethylbutyl) hydroquinone
Hardener = bis(vinylsulphonyl) methane (BVSM)

Samples were prepared using the same underlying layers, varying only the overcoat composition as specified in the table below. The drying conditions in the drying section of the coating machine were adjusted to control the average web temperature from the point at which the coating is an average of 15% gelatin to the point where it is 65% gelatin. This is reported as the drying temperature in the table below, where a higher temperature is harsher.

Samples of coating elements were processed and evaluated as in Example 5.

| Sample | | Drying Temperature | Gel Type | Gelatin Laydown | Silica Laydown | % silica | SF-1 | SF-2 | SF-12 | SF-13 |
|---|---|---|---|---|---|---|---|---|---|---|
| 13 | Comp | 69 | C | 0.6456 | 0.1614 | 20 | 0.0080 | 0.0033 | | |
| 14 | Inv | 69 | H | 0.6456 | 0.1614 | 20 | 0.0080 | 0.0033 | | |
| 12 | Inv | 69 | K | 0.6456 | 0.1614 | 20 | 0.0080 | 0.0033 | | |
| 19 | Inv | 69 | K | 0.6456 | 0.1614 | 20 | 0.0080 | 0.0033 | | |
| 15 | Inv | 69 | K | 0.6456 | 0.1614 | 20 | 0.0080 | | 0.0033 | |
| 16 | Inv | 69 | K | 0.6456 | 0.1614 | 20 | 0.0080 | | | 0.0033 |
| 17 | Comp | 69 | C | 0.5651 | 0.2422 | 30 | 0.0080 | 0.0024 | 0.0039 | |
| 18 | Inv | 69 | K | 0.5651 | 0.2422 | 30 | 0.0080 | 0.0024 | 0.0039 | |
| 42 | Comp | 71 | C | 0.6456 | 0.1614 | 20 | 0.0080 | 0.0033 | | |
| 43 | Inv | 71 | H | 0.6456 | 0.1614 | 20 | 0.0080 | 0.0033 | | |
| 44 | Inv | 71 | K | 0.6456 | 0.1614 | 20 | 0.0080 | 0.0033 | | |
| 45 | Inv | 71 | K | 0.6456 | 0.1614 | 20 | 0.0080 | | 0.0033 | |
| 46 | Inv | 71 | K | 0.6456 | 0.1614 | 20 | 0.0080 | | | 0.0033 |
| 47 | Comp | 71 | C | 0.5651 | 0.2422 | 30 | 0.0080 | 0.0024 | 0.0039 | |
| 41 | Inv | 71 | K | 0.5651 | 0.2422 | 30 | 0.0080 | 0.0024 | 0.0039 | |

Results

| Sample | | Drying Temperature | Gel Type | % silica | Gloss 3D | Gloss 7D | Gloss 14D | Haze 3D | Haze 7D | Haze 14D | Reticulation 3D | Reticulation 7D | Reticulation 14D |
|---|---|---|---|---|---|---|---|---|---|---|---|---|---|
| 13 | Comp | 69 | C | 20 | 65.8 | 68.5 | 67.5 | 24.6 | 23 | 23.3 | 3 | 4 | 3 |
| 14 | Inv | 69 | H | 20 | 67.4 | 68.1 | 68.9 | 24.3 | 24.3 | 23.2 | 3 | 3 | 3 |
| 12 | Inv | 69 | K | 20 | 66.4 | 67.1 | 69.1 | 24.9 | 24.6 | 22.8 | 3 | 3 | 3 |
| 19 | Inv | 69 | K | 20 | 64.4 | 67.2 | 67.1 | 26.4 | 24.8 | 24.6 | 3 | 4 | 3 |
| 15 | Inv | 69 | K | 20 | 66.6 | 69 | 68.8 | 24.7 | 23.4 | 23.4 | 3 | 3 | 3 |
| 16 | Inv | 69 | K | 20 | 65.3 | 67.8 | 68.5 | 26 | 22.1 | 23.8 | 3 | 4 | 3 |
| 17 | Comp | 69 | C | 30 | 63.8 | 64.8 | 65.5 | 25.4 | 24 | 23.5 | 3 | 3 | 3 |
| 18 | Inv | 69 | K | 30 | 64.8 | 66 | 67.6 | 25.2 | 24.9 | 22.9 | 3 | 3 | 3 |
| 42 | Comp | 71 | C | 20 | 53.3 | 56.8 | 63.1 | 33.3 | 31.2 | 27 | 5 | 5 | 5 |
| 43 | Inv | 71 | H | 20 | 55.3 | 62.7 | 64.4 | 32.9 | 27.8 | 26.3 | 4 | 5 | 4 |
| 44 | Inv | 71 | K | 20 | 49.9 | 53.4 | 56.8 | 35.8 | 33.4 | 30.7 | 5 | 5 | 5 |
| 45 | Inv | 71 | K | 20 | 56 | 60.2 | 60.8 | 31.7 | 28.5 | 27.6 | 4 | 5 | 5 |
| 46 | Inv | 71 | K | 20 | 44.8 | 48.7 | 50.5 | 38.9 | 36 | 35 | 5 | 5 | 5 |

-continued

| Sample | | Drying Temperature | Gel Type | % silica | Gloss 3D | Gloss 7D | Gloss 14D | Haze 3D | Haze 7D | Haze 14D | Reticulation 3D | Reticulation 7D | Reticulation 14D |
|---|---|---|---|---|---|---|---|---|---|---|---|---|---|
| 47 | Comp | 71 | C | 30 | 49.7 | 59.3 | 58.1 | 28.3 | 25 | 24.4 | 3 | 5 | 3 |
| 41 | Inv | 71 | K | 30 | 60.4 | 63.7 | 64.2 | 28.5 | 26.3 | 25.6 | 4 | 5 | 4 |

The data in this example show that higher gloss can generally be achieved using the gelatin of the invention, regardless of the surfactant combination used. Under harsh drying conditions resulting in a drying temperature of 71° F. (22° C.) and with high silica loading, the gelatin of the invention exhibits gloss and haze most similar to all the variations at 69° F. (22° C.), indicating may enable faster coating speeds and increase productivity.

EXAMPLE 7

Elements were prepared as above except that the acid-processed gelatin the supercoat of elements was replaced by acid-processed poultry gelatin H. The coating solution for the supercoat of element was prepared with 20% less water than coating fluid J.

The samples were processed and gloss and haze were measured as in Example 5 above.

| Element | Overcoat gelatin | Days after Coating | Gloss | Haze |
|---|---|---|---|---|
| 701 | C | 3 | 67.9 | 22.5 |
| 702 | H | 3 | 71.1 | 19.3 |
| 701 | C | 7 | 69.4 | 21.8 |
| 702 | H | 7 | 72.9 | 19.3 |
| 701 | C | 14 | 72.15 | 18.95 |
| 702 | H | 14 | 71.05 | 20.1 |

Coating elements with the gelatin H of the invention show improved gloss and haze versus the comparison with acid-processed bovine gelatin C of the prior art. The viscosity of the coating melt containing gelatin H had a viscosity that was better matched to the underlying UV layer, and exhibited exceptional stability with time.

The invention has been described in detail with particular reference to be certain preferred embodiments thereof, but it will be understood that variations and modifications can be effected within the spirit and scope of the invention.

What is claimed is:

1. An aqueous coating composition comprising poultry gelatin and further comprising colloidal silica.

2. The aqueous coating composition of claim 1 wherein said poultry gelatin is present in an amount of less than 25 wt %.

3. The aqueous coating composition of claim 1 wherein said colloidal silica is present in an amount between 10 and 40% by weight of the total gelatin and colloidal silica amount in said coating composition.

4. The aqueous coating composition of claim 1 wherein said coating composition further comprises sulfo succinate surfactant.

5. The aqueous coating composition of claim 1 wherein said coating composition further comprises polymeric latex particles.

6. The aqueous coating composition of claim 1 wherein said coating composition further comprises naphthalene sulfonate.

7. The aqueous coating composition of claim 1 wherein said coating composition further comprises bovine gelatin.

8. The aqueous coating composition of claim 1 wherein said poultry gelatin has an isoelectric point greater than 7.5.

9. The aqueous coating composition of claim 1 wherein said coating composition further comprises a lubricant dispersion.

10. The aqueous coating composition of claim 1 wherein said coating composition further comprises a lubricant dispersion wherein said lubricant dispersion comprises polydimethylsiloxane.

11. The aqueous coating composition of claim 9 wherein said lubricant dispersion has a particle size of less than 0.6 micrometers or greater than 3 micrometers.

12. An aqueous coating composition comprising poultry gelatin, wherein said coating composition further comprises polymeric latex particles.

13. The aqueous coating composition of claim 12 wherein said poultry gelatin is present in an amount of less than 25 wt %.

14. The aqueous coating composition of claim 12 wherein said coating composition further comprises sulfo succinate surfactant.

15. The aqueous coating composition of claim 12 wherein said coating composition further comprises naphthalene sulfonate.

16. The aqueous coating composition of claim 12 wherein said coating composition further comprises bovine gelatin.

17. The aqueous coating composition of claim 12 wherein said poultry gelatin has an isoelectric point greater than 7.5.

18. The aqueous coating composition of claim 12 wherein said coating composition further comprises a lubricant dispersion.

19. The aqueous coating composition of claim 18 wherein said lubricant dispersion has a particle size of less than 0.6 micrometers or greater than 3 micrometers.

20. An aqueous coating composition comprising poultry gelatin, wherein said coating composition further comprises a lubricant dispersion wherein said lubricant dispersion comprises polydimethylsiloxane.

21. The aqueous coating composition of claim 20 wherein said poultry gelatin is present in an amount of less than 25 wt %.

22. The aqueous coating composition of claim 20 wherein said coating composition further comprises sulfo succinate surfactant.

23. The aqueous coating composition of claim 20 wherein said coating composition further comprises naphthalene sulfonate.

24. The aqueous coating composition of claim 20 wherein said coating composition further comprises bovine gelatin.

25. The aqueous coating composition of claim 20 wherein said poultry gelatin has an isoelectric point greater than 7.5.

26. The aqueous coating composition of claim 20 wherein said lubricant dispersion has a particle size of less than 0.6 micrometers or greater than 3 micrometers.

* * * * *